US011518722B2

United States Patent
Wang et al.

(10) Patent No.: US 11,518,722 B2
(45) Date of Patent: Dec. 6, 2022

(54) METHOD FOR PREPARATION OF NANOCERIA SUPPORTED ATOMIC NOBLE METAL CATALYSTS AND THE APPLICATION OF PLATINUM SINGLE ATOM CATALYSTS FOR DIRECT METHANE CONVERSION

(71) Applicant: THE JOHNS HOPKINS UNIVERSITY, Baltimore, MD (US)

(72) Inventors: Chao Wang, Ellicott City, MD (US); Pengfei Xie, Baltimore, MD (US); Tiancheng Pu, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/971,562

(22) PCT Filed: Feb. 19, 2019

(86) PCT No.: PCT/US2019/018480
§ 371 (c)(1),
(2) Date: Aug. 20, 2020

(87) PCT Pub. No.: WO2019/164797
PCT Pub. Date: Aug. 29, 2019

(65) Prior Publication Data
US 2020/0392054 A1 Dec. 17, 2020

Related U.S. Application Data

(60) Provisional application No. 62/632,483, filed on Feb. 20, 2018.

(51) Int. Cl.
*B01J 23/10* (2006.01)
*B01J 23/38* (2006.01)
(Continued)

(52) U.S. Cl.
CPC .............. *C07C 2/84* (2013.01); *B01J 23/10* (2013.01); *B01J 23/38* (2013.01); *B01J 23/42* (2013.01);
(Continued)

(58) Field of Classification Search
None
See application file for complete search history.

(56) References Cited

U.S. PATENT DOCUMENTS

2015/0080614 A1* 3/2015 Rajaram .............. B01J 37/0018
568/835
2016/0318804 A1* 11/2016 Cho ........................ C04B 35/64
(Continued)

FOREIGN PATENT DOCUMENTS

CN 104628511 A 5/2015
CN 106475096 A 3/2017

OTHER PUBLICATIONS

Aldrich, Cerium (IV) oxide—nanopowder Product Specification, obtained online, 2022 (Year: 2022).*
(Continued)

*Primary Examiner* — Philip Y Louie
(74) *Attorney, Agent, or Firm* — MH2 Technology Law Group LLP

(57) ABSTRACT

Described are methods for converting methane to olefins, aromatics, or a combination thereof using a single atom catalyst comprising $CeO_2$ nanoparticles impregnated with individual atoms of noble metals including Pt, Pd, Rh, Ru, Ag, Au, Ir, or a combination thereof. These single atom catalysts of the present invention are heated with methane to form olefins and aromatics.

10 Claims, 18 Drawing Sheets

(51) Int. Cl.

| | |
|---|---|
| *B01J 23/42* | (2006.01) |
| *B01J 35/10* | (2006.01) |
| *C07C 2/84* | (2006.01) |
| *B01J 35/00* | (2006.01) |
| *B01J 37/04* | (2006.01) |
| *B01J 37/08* | (2006.01) |
| *B01J 37/10* | (2006.01) |
| *C10G 45/70* | (2006.01) |
| *C10G 50/00* | (2006.01) |

(52) U.S. Cl.
CPC ....... *B01J 35/0013* (2013.01); *B01J 35/1009* (2013.01); *B01J 35/1014* (2013.01); *B01J 37/04* (2013.01); *B01J 37/088* (2013.01); *B01J 37/10* (2013.01); *C10G 45/70* (2013.01); *C10G 50/00* (2013.01); *C07C 2523/10* (2013.01); *C07C 2523/63* (2013.01); *C10G 2400/22* (2013.01); *C10G 2400/30* (2013.01)

(56) References Cited

U.S. PATENT DOCUMENTS

| | | | |
|---|---|---|---|
| 2016/0346762 A1 | 12/2016 | Qu et al. | |
| 2018/0056276 A1* | 3/2018 | Xiao | ........................ B01J 23/44 |
| 2019/0126252 A1* | 5/2019 | Nie | ....................... B01J 35/1014 |
| 2019/0296366 A1* | 9/2019 | Yoon | .................... H01M 4/8605 |
| 2020/0016534 A1* | 1/2020 | Ding | ......................... B01J 37/04 |

OTHER PUBLICATIONS

International Search Report and Written Opinion in corresponding International Application No. PCT/US2019/018480 dated May 30, 2019, 8 pages.
Aleksandrov et al., "Can the state of platinum species be unambiguously determined by the stretching frequency of an adsorbed CO probe molecule?", Phys. Chem. Chem. Phys., 2016, vol. 18, 14 pages.
Asokan et al., "Using probe molecule FTIR spectroscopy to identify and characterize Pt-group metal based single atom catalysts", Chinese Journal of Catalysis, 2017, vol. 38, 8 pages.
Chin et al., "Reactivity of Chemisorbed Oxygen Atoms and Their Catalytic Consequences during CH4O2 Catalysis on Supported Pt Clusters", Journal of the American Chemical Society, 2011, vol. 133, 21 pages.
Duarte et al., "Structure, Activity, and Stability of Atomically Dispersed Rh in Methane Steam Reforming", ACS Catalysis, Mar. 12, 2014, vol. 4, 8 pages.
Dvorak et al., "Creating single-atom Pt-ceria catalysts by surface step decoration", Nature Communications, Feb. 24, 2016, 8 pages.
Economides et al., "The state of natural gas", Journal of Natural Gas Science and Engineering, 2009, vol. 1, 13 pages.
Flytzani-Stephanopoulos, "Supported metal catalysts at the single-atom limit—A viewpoint", Chinese Journal of Catalysis, 2017, vol. 38, 11 pages.
Galvis et al., "Supported Iron Nanoparticles as Catalysts for Sustainable Production of Lower Olefins", SCIENCE, Feb. 17, 2012, vol. 335, 5 pages.
Guo et al., "Direct, Nonoxidative Conversion of Methane to Ethylene, Aromatics, and Hydrogen", SCIENCE, May 9, 2014, vol. 344, 5 pages.
Jones et al., "Thermally stable single-atom platinum-on-ceria catalysts via atom trapping", SCIENCE, Jul. 8, 2016, vol. 353, Issue 6295, 6 pages.
Keller et al., "Synthesis of Ethylene via Oxidative Coupling of Methane.", Journal of Catalysis, 1982, vol. 73, 11 pages.
Kim et al., "n-Heptane hydroisomerization over Pt/MFI zeolite nanosheets: Effects of zeolite crystal thickness and platinum location", Journal of Catalysis, 2013, vol. 301, 11 pages.
Lei et al., "Surface-Structure Sensitivity of CeO2 Nanocrystals in Photocatalysis and Enhancing the Reactivity with Nanogold", ACS Catalysis, Jun. 5, 2015, 9 pages.
Li et al., "Shape-Controlled CeO2 Nanoparticles: Stability and Activity in the Catalyzed HCI Oxidation Reaction", ACS Catalysis, Aug. 11, 2017, vol. 7, 11 pages.
Liang et al., "Catalytically Stable and Active CeO2 Mesoporous Spheres", Inorganic Chemistry, 2010, vol. 49, 3 pages.
Lin et al., "Remarkable Performance of Ir1/FeOx Single-Atom Catalyst in Water Gas Shift Reaction", Journal of the American Chemical Society, Oct. 3, 2013, vol. 135, 4 pages.
Liu, "Catalysis by Supported Single Metal Atoms", ACS Catalysis, Oct. 18, 2016, vol. 7, 26 pages.
Liu et al., "Bifunctional Catalysis of Mo/HZSM-5 in the Dehydroaromatization of Methane to Benzene and Naphthalene XAFS/TG/DTA/MASS/FTIR Characterization and Supporting Effects", Journal of Catalysis, 1999, vol. 181, 14 pages.
Liu et al., "Generation of subnanometric platinum with high stability during transformation of a 2D zeolite into 3D", Nature Materials, 2016, vol. 16, 10 pages.
Lucci et al., "Selective hydrogenation of 1,3-butadiene on platinum-copper alloys at the single-atom limit", Nature Communications, Oct. 9, 2015, 8 pages.
Manto et al., "Catalytic Dephosphorylation Using Ceria Nanocrystals", ACS Catalysis, Feb. 1, 2017, vol. 7, 8 pages.
Matin et al., "Rational syntheses of core-shell Fe@(PtRu) nanoparticle electrocatalysts for the methanol oxidation reaction with complete suppression of CO-poisoning and highly enhanced activity", Journal of Materials Chemistry A, 2015, vol. 3, 11 pages.
Mazumder et al., "Oleylamine-Mediated Synthesis of Pd Nanoparticles for Catalytic Formic Acid Oxidation", JACS Communications, 2009, vol. 131, 2 pages.
McFarland, "Unconventional Chemistry for Unconventional Natural Gas", SCIENCE, Oct. 19, 2012, vol. 338, 4 pages.
Mesters, "A Selection of Recent Advances in C1 Chemistry", The Annual Review of Chemical and Biomolecular Engineering, 2016, vol. 7, 19 pages.
Morejudo et al., "Direct conversion of methane to aromatics in a catalytic co-ionic membrane reactor", SCIENCE, Aug. 5, 2016, vol. 353, Issue 6299, 5 pages.
Moscu et al., "Direct evidence by in situ IR CO monitoring of the formation and the surface segregation of a Pt—Sn alloy", Chem. Commun., 2014, vol. 50, 3 pages.
Ohnishi et al., "Catalytic Dehydrocondensation of Methane with CO and CO2 toward Benzene and Naphthalene on Mo/HZSM-5 and Fe/Co-Modified Mo/HZSM-5", Journal of Catalysis, 1999, vol. 182, 12 pages.
Parkinson, "Unravelling single atom catalysis: The surface science approach", Chinese Journal of Catalysis, 2017, vol. 38, 6 pages.
Qiao et al.,"Single-atom catalysis of COoxidation using Pt1/FeOx", Nature Chemistry, Aug. 2011, vol. 3, 8 pages.
Saha et al., "Postextraction Separation, On-Board Storage, and Catalytic Conversion of Methane in Natural Gas: A Review", Chemical Reviews, 2016, vol. 116, 64 pages.
Sattler et al., "Platinum-Promoted Ga/Al2O3 as Highly Active, Selective, and Stable Catalyst for the Dehydrogenation of Propane", Angew. Chem. Int. Ed., 2014, vol. 53, 6 pages.
Sattler et al., "Catalytic Dehydrogenation of Light Alkanes on Metals and Metal Oxides", Chemical Reviews, Aug. 27, 2014, vol. 114, 41 pages.
Schwach et al.,"Direct Conversion of Methane to Value-Added Chemicals over Heterogeneous Catalysts: Challenges and Prospects", Chemical Reviews, May 5, 2017, vol. 117, 24 pages.
Shah et al., "Production of Hydrogen and Carbon Nanostructures by Non-oxidative Catalytic Dehydrogenation of Ethane and Propane", Energy & Fuels, 2004, vol. 18, 9 pages.
Sun et al., "Novel Pt/Mg(In)(Al)O catalysts for ethane and propane dehydrogenation", Journal of Catalysis, 2011, vol. 282, 10 pages.
Vajda et al., "Subnanometre platinum clusters as highly active and selective catalysts for the oxidative dehydrogenation of propane", Nature Materials, Mar. 2009, vol. 8, 4 pages.
Wang, et al., "Dehydrogenation and aromatization of methane under non-oxidizing conditions". Catalysis Letters, 1993, vol. 21, 7 pages.

(56) References Cited

OTHER PUBLICATIONS

Wood et al., "Gas-to-liquids (GTL): A review of an industry offering several routes for monetizing natural gas", Journal of Natural Gas Science and Engineering, 2012, vol. 9, 13 pages.

Yang et al., "Single-Atom Catalysts: A New Frontier in Heterogeneous Catalysis", Accounts of Chemical Research, 2013, vol. 46, No. 8, 9 pages.

Yang et al., "Atomically Dispersed Au-(OH)x Species Bound on Titania Catalyze the Low-Temperature Water-Gas Shift Reaction", Journal of The American Chemical Society, Feb. 25, 2013, vol. 135, 4 pages.

Zecevic, et al. "Heterogeneities of the Nanostructure of Platinum/Zeolite Y Catalysts Revealed by Electron Tomography". ACSNANO, 2013, vol. 7, No. 4, 8 pages.

Zhang et al., "One-Pot Synthesis of Platinum-Ceria/Graphene Nanosheet as Advanced Electrocatalysts for Alcohol Oxidation", CHEMELECTROCHEM Articles, 2015, vol. 2, 9 pages.

Zhang et al., "Oxygen vacancies on nanosized ceria govern the NOx storage capacity of NSR catalysts", Catalysis Science &Technology, 2016, vol. 6, 13 pages.

Zhang et al., "Thermally stable single atom Pt/m-Al2O3 for selective hydrogenation and CO oxidation", Nature Communications, Jul. 27, 2017, 10 pages.

Zhu et al., "Sulfur as a selective 'soft' oxidant for catalytic methane conversion probed by experiment and theory", Mature Chemistry, Feb. 2013, vol. 5, 6 pages.

\* cited by examiner

METHOD FOR PREPARATION OF NANOCERIA SUPPORTED ATOMIC NOBLE METAL CATALYSTS AND THE APPLICATION OF PLATINUM SINGLE ATOM CATALYSTS FOR DIRECT METHANE CONVERSION

REFERENCE TO RELATED APPLICATIONS

This application is a national stage entry from International Application No. PCT/US2019/018480, filed on Feb. 19, 2019, published as International Publication No. WO 2019/164797 A1 on Aug. 29, 2019, and claims the benefit of U.S. Provisional Patent application 62/632,483, filed Feb. 20, 2018, all of which are hereby incorporated by reference in their entirety for all purposes as if fully set forth herein.

STATEMENT OF GOVERNMENTAL INTEREST

This invention was made with government support under grant no. DE-AR0000708 awarded by the Department of Energy. The government has certain rights in the invention.

BACKGROUND OF THE INVENTION

Over the recent years, natural gas has risen as a clean and cost-effective source of hydrocarbons, with great potential for replacing coal and crude oil in many sectors of energy and chemical industries. The conventional approaches for conversion and utilization of methane via syngas (a mixture of CO and $H_2$) is however challenged by the low carbon efficiency, large loss of exergy and high capital cost associated with the complex, multistage processes. Alternatively, direct conversion of methane can be achieved via oxidative coupling or non-oxidative dehydrogenation to produce olefins or aromatics. These approaches are believed to be more economical and environment-friendly than via the syngas.

Single atom catalysts (SACs) represent a new frontier of heterogeneous catalysis and have been demonstrated to exhibit enhanced catalytic activity and selectivity in many reactions, including CO oxidation, water-gas shift, methane steam reforming, selective hydrogenation of alkynes and dienes and so on. The superior catalytic performance can be attributed to the atomic dispersion of metal atoms with low coordination number, quantum confinement and/or strong metal-support (mostly metal oxides) interactions. It has also been reported that atomic Fe sites embedded in a silica matrix give rise to high catalytic selectivity for the non-oxidative conversion of methane to ethylene, aromatics and hydrogen; the absence of metal ensembles suppresses C—C coupling and carbon coking, giving rise to long-term stability under the high-temperature reaction conditions. Nevertheless, co-presence (or formation under reaction conditions at high temperatures) of sub-nm clusters and nanoscale particles have been found in many SACs, which remains a challenge for the synthesis and understanding the catalytic mechanisms of atomic catalysts. It is also rare that one synthesis method can be applied to various metals to form single atom catalysts. The techniques disclosed in the present patent include the synthesis method of preparing single atom noble metal catalysts supported on $CeO_2$ including Pt, Pd, Rh, Ru, Ag, Au and Ir. Single atom Pt supported on $CeO_2$ was tested in direct nonoxidative methane conversion to light olefins and aromatics with superior performance and stability. All noble metal single atom catalysts have been characterized with DRIFTS of CO adsorption to demonstrate the sore existence of single atom without the presence of clusters or nanoparticles on $CeO_2$.

Definitions

"Pt" refers to Platinum, "Pd" refers to Palladium, "Rh" refers to Rhodium, "Ru" refers to Ruthenium, "Ag" refers to Silver, "Au" refers to Gold and "Ir" refers to Iridium.

"SACs" refers to single atom catalysts.

TEM refers to transmission electron microscopy.

HAADF-STEM refers to high angle annular dark field-scanning transmission electron microscopy.

XPS refers to X-ray photoelectron spectroscopy.

DRIFTS refers to diffuse reflectance infrared fourier transform spectroscopy.

XRD refers to X-ray diffraction.

BET refers to Brunauer-Emmett-Teller theory.

All single atom noble metal catalysts supported on $CeO_2$ which were claimed in the present patent is written in "$M_1@CeO_2$", where "M" refers to this specific metal.

Other catalysts used for comparison and/or in the processed of formation of single atom catalyst are written in "$M/CeO_2$", where "M" refers to this specific metal.

SUMMARY OF THE INVENTION

One embodiment of the present invention is a method for converting methane to olefins, aromatics, or a combination thereof. The steps include providing a single atom catalyst comprising $CeO_2$ nanoparticles impregnated with a noble metal atom; adding methane; increasing the temperature to a range of 700° C. to 1200° C., 800° C. to 1100° C., or 900° C. to 1000° C., and forming olefins, aromatics, or a combination thereof. The $CeO_2$ nanoparticles of the present invention are heated for 30 minutes to 2 hours, 45 minutes to 1½ hours; or 1 hour to 1½ hours, as examples of heating durations. The heating of the $CeO_2$ nanoparticles of the present invention may occur by any means such as a bed flow reactor. The methods of the present invention may include an additional step of preheating the single atom catalyst at a temperature in the range of 15° C. to 500° C., 25° C. to 450° C., 50° C. to 400° C., 75° C. to 300° C., or 100° C. to 200° C. prior to the addition of methane. The methods of the present invention may have a methane conversion in the range of 10% to 30%; 15% to 30%; 15% to 25%; or 17% to 24%. The methods of the present invention have a coke selectivity below 15%; 14%; 13%; 12%; 11%; 10%; 9%; 8%; 7%; 6%; 5%; 4%; 3%; 2%; or 1%. The methods of the present invention may have a $C_2$ productivity of greater than 50%; 60%; 70%; 80%; 90%; or 95%. Noble metals are used in the present invention such as Pt, Pd, Rh, Ru, Ag, Au, Ir, or a combination thereof, as examples.

Another embodiment of the present invention is a method of making a single atom catalyst. The steps include dissolving $Ce(NO_3)_3$ with a noble metal, or a precursor of a noble metal, in water and an organic surfactant selected from the group comprising ethylene glycol, propionic acid, or a combination thereof, to form a mixture; hydrothermal synthesis of the mixture to form $CeO_2$ porous nanospheres comprising incorporated noble metal clusters; removing the water and the organic surfactant from the $CeO_2$ porous nanospheres; calcinating the $CeO_2$ porous nanospheres to convert them into crystalline nanoslabs comprising atomically dispersed noble metal; and forming one or more single atom catalysts. The step of hydrothermal synthesis occurs under a temperature in the range of 100° C. to 250° C.; 125°

C. to 225° C.; 150° C. to 200° C.; or 155° C. to 170° C., as examples. The step of calcinating occurs at a temperature in the range of 700° C. to 1500° C.; 800° C. to 1400° C.; 850° C. to 1300° C.; or 900° C. to 1200° C., as examples. Noble metals are used in the present invention such as Pt, Pd, Rh, Ru, Ag, Au, Ir, or a combination thereof, as examples. An example of a precursor of a noble metal used in the present invention is a noble metal salt such as $PtCl_4$, $Pd(NO_3)_2$, $RhCl_3$, $AgNO_3$, $AuCl_3$, $IrCl_3$, or a combination thereof. A noble metal used in the present invention may be in an oxidize form. For example ($Pt^{2+}$), the oxidized form of Pt may be used in the methods of the present invention.

Another embodiment of the present invention is a single atom catalyst comprising $CeO_2$ nanoparticles impregnated with individual noble metal atoms. Noble metal atoms are part of the catalysts. For example, Pt atoms, Pd atoms, Rh atoms, Ru atoms, Ag atoms, Au atoms, Ir atoms, or a combination thereof may be part of $CeO_2$ nanoparticles of the present invention. A single atom catalyst of the present invention may comprise a specific surface area in the range of 5 $m^2/g$ to 40 $m^2/g$; 10 $m^2/g$ to 35 $m^2/g$; 15 $m^2/g$ to 30 $m^2/g$; 18 $m^2/g$ to 25 $m^2/g$, as examples. A single atom catalyst of the present invention may comprise binding energies in the range of 40 eV to 100 eV; 50 eV to 90 eV; 60 eV to 80 eV, or 70 eV to 80 eV, as examples.

Unless defined otherwise, all technical and scientific terms used herein have the meaning commonly understood by a person skilled in the art to which this invention belongs.

DETAILED DESCRIPTION OF THE INVENTION

The inventors have discovered the synthesis of ceria ($CeO_2$)-supported atomic Pt catalysts for direct conversion of methane into light hydrocarbons. Pt has been widely used to active the C—H bond in hydrocarbons, but carbon coking usually takes place on the conventional catalysts composed of Pt clusters or nanoparticles at high temperatures (e.g., >800° C.), which has limited the application of Pt-based catalysts for methane conversion. In this study, nanoceria-supported atomic Pt catalysts were synthesized by calcination of Pt-impregnated porous $CeO_2$ nanoparticles at high temperature (ca. 1,000° C.) (see Methods/Examples). The obtained $Pt_1@CeO_2$ catalyst was characterized by using HAADF-STEM and XPS, and the absence of Pt ensembles was further confirmed by DRIFTS analysis using CO as a molecular probe. The $Pt_1@CeO_2$ catalyst was then evaluated for the methane conversion reaction, and the catalytic performance was further compared to the control catalyst prepared by depositing Pt nanoparticles on similar $CeO_2$ substrates.

Figure 1A:
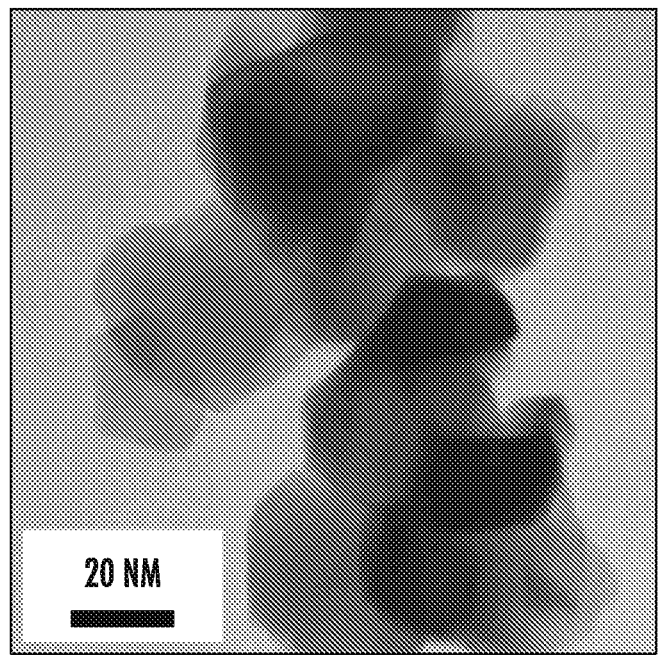
FIG. 1A-1F. Representative (a) TEM and (b-d) HAADF-STEM images of the $Pt_1@CeO_2$ catalyst with 0.5 wt % of Pt. (e, f) Intensity profiles associated with the line scans marked in (d).
Figure 1B:
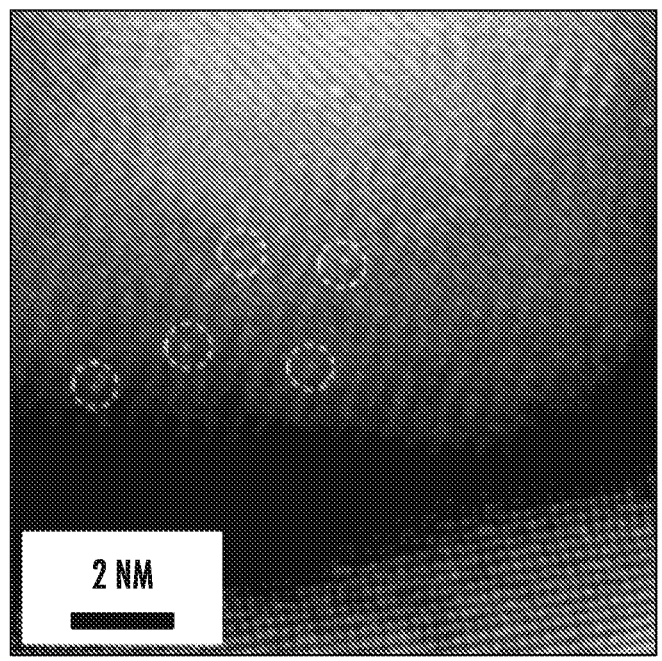
Figure 1C:
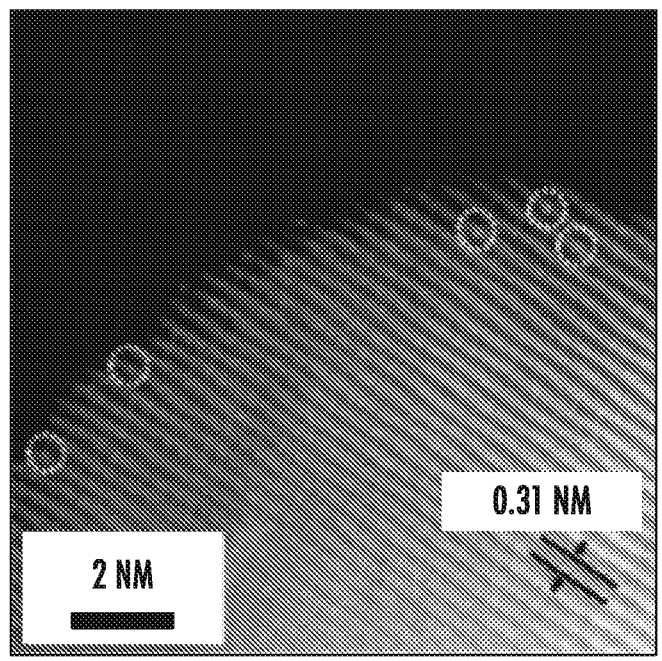
Figure 1D:
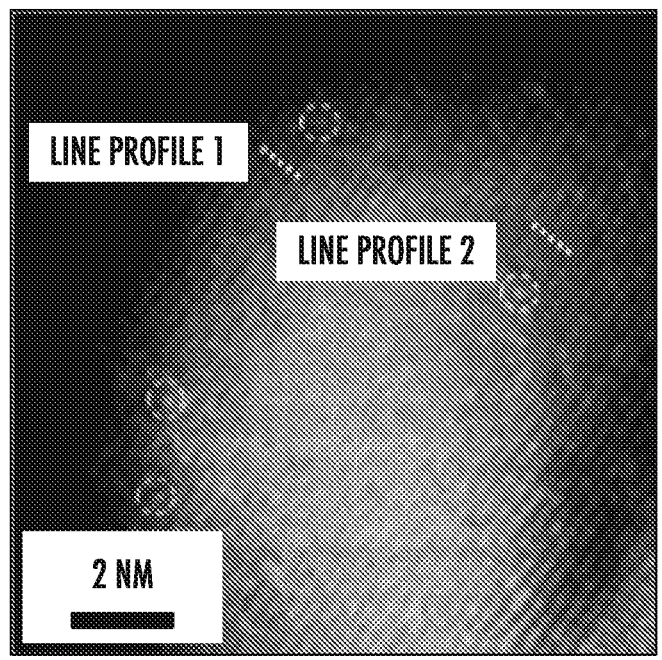
Figure 1E:
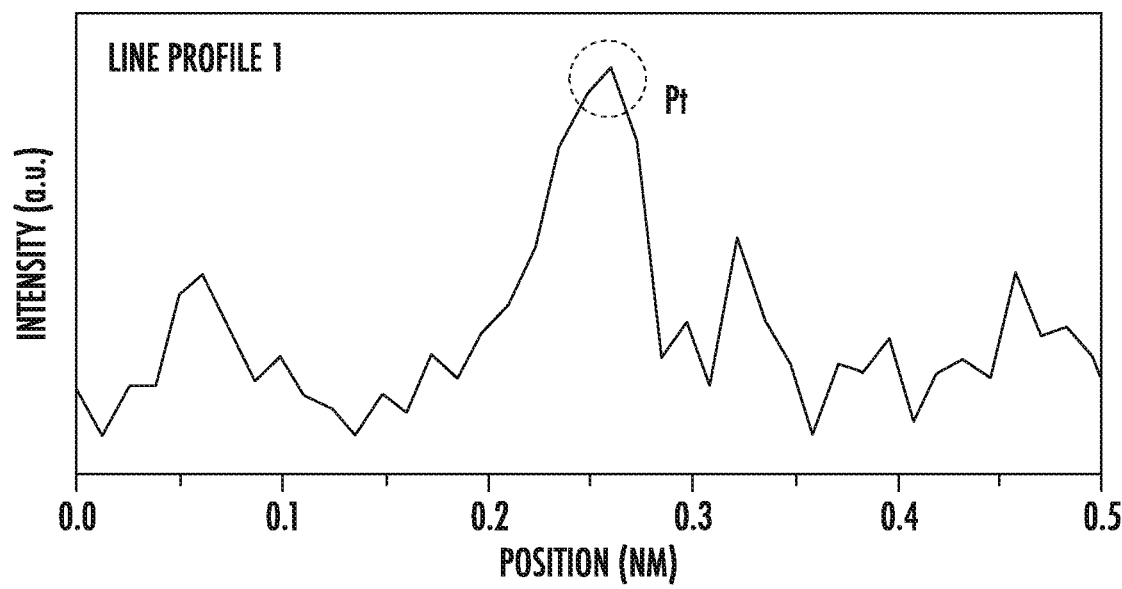
Figure 1F:
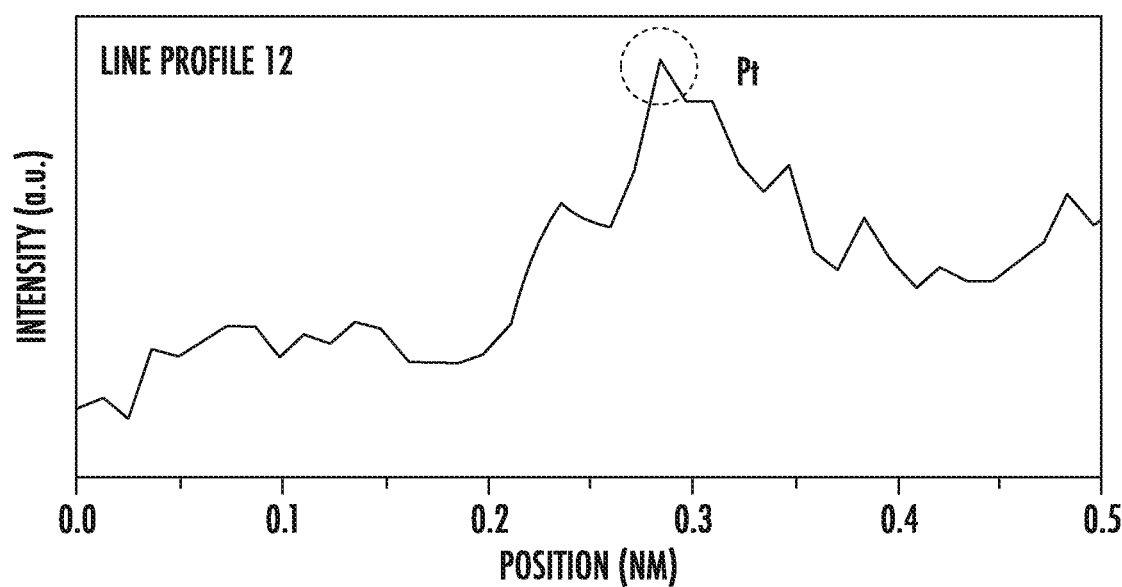
Figure 2A:
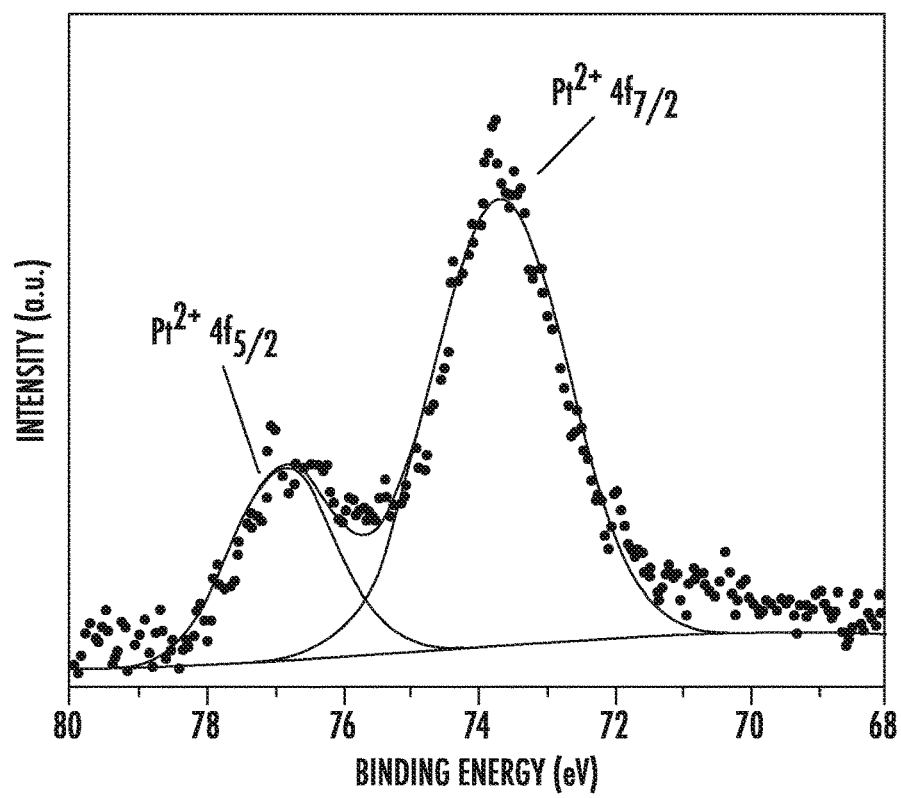
FIG. 2A-2D. XPS spectra collected on the (a, b) $Pt_1@CeO_2$ and (c, d) $PtNPs/CeO_2$ catalysts at the (a, c) Pt 4f and (b, d) Ce 3d edges.
Figure 2B:
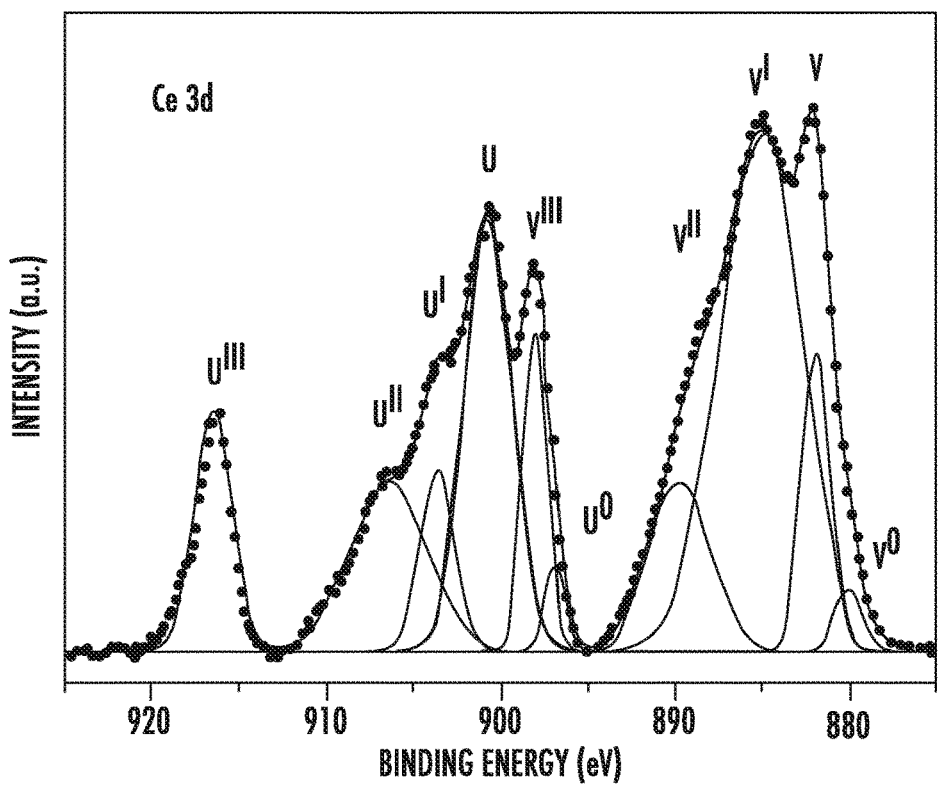
Figure 2C:
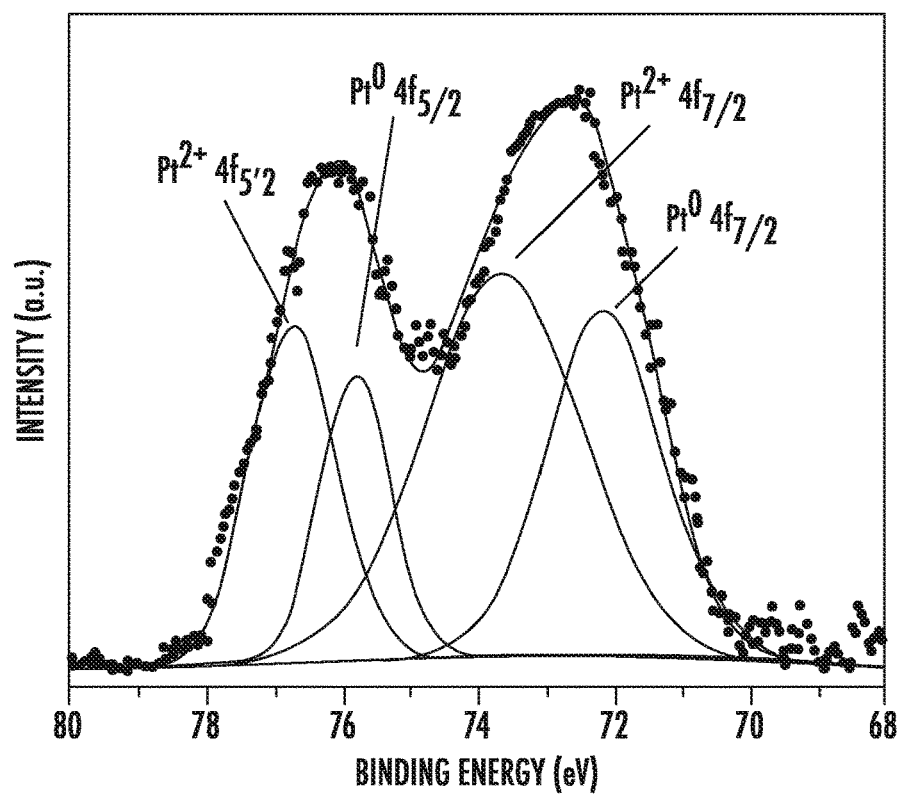
Figure 2D:
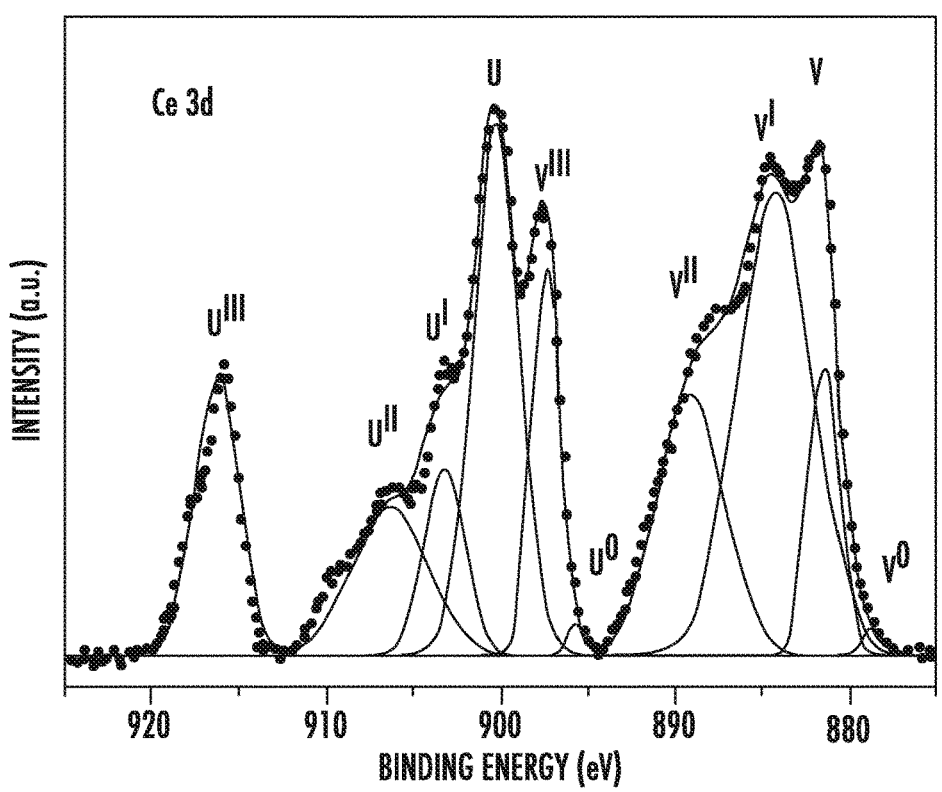
Figure 8:
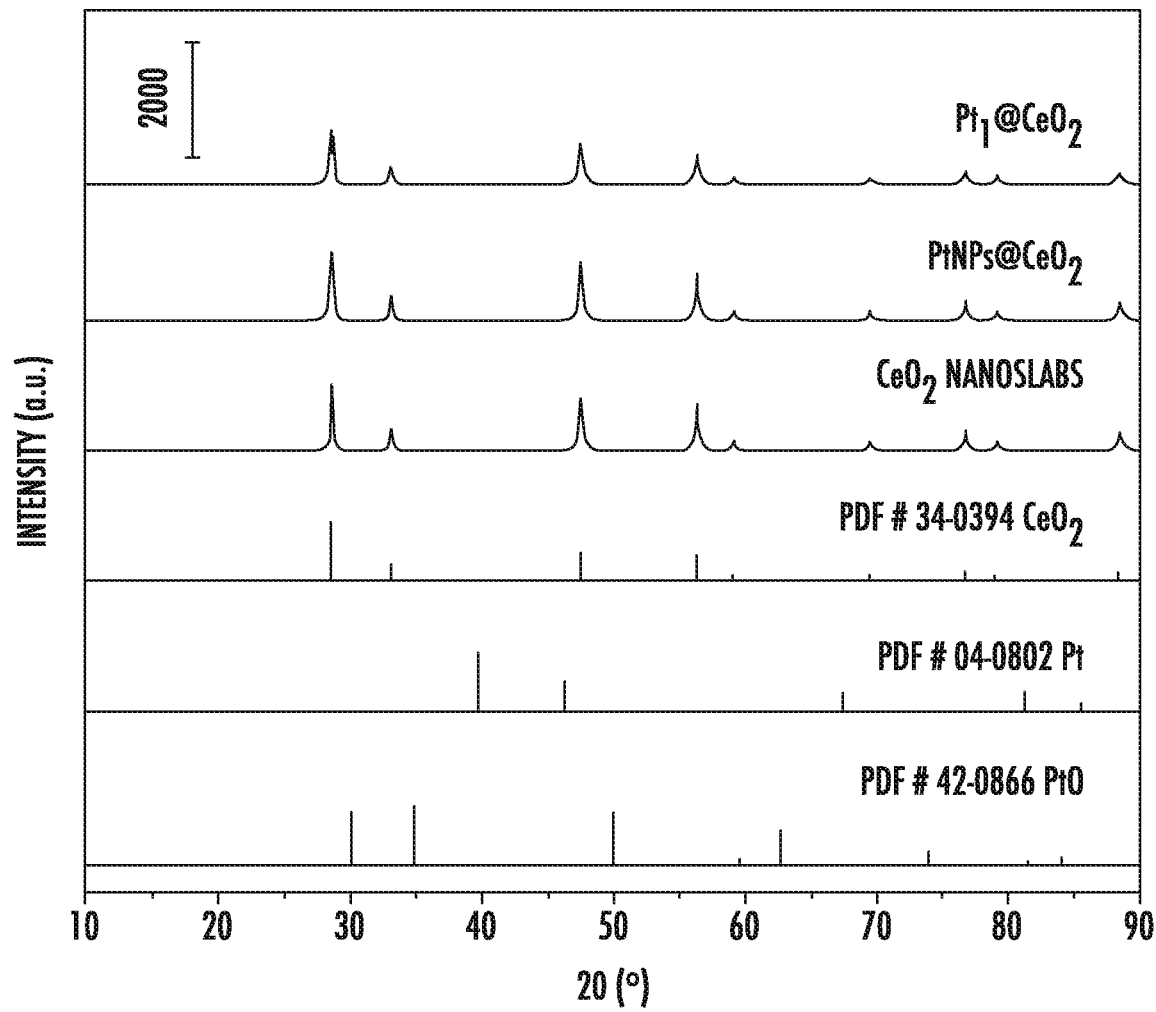
FIG. 8. XRD patterns of $CeO_2$ nanoslabs, $PtNPs/CeO_2$ and $Pt_1@CeO_2$.

FIG. 1a shows the representative transmission electron microscopy (TEM) image of the as-synthesized $Pt_1@CeO_2$ catalyst. The catalyst particles exhibit a slab-like morphology with the size varying from ~15 to ~40 nm. HAADF-STEM images reveal that the obtained catalyst possesses atomic Pt dispersed on $CeO_2$ nanoslabs (FIGS. 1 b-d). In these images, individual Pt atoms are exhibited as bright dots with higher contrast than the surrounding $CeO_2$ lattice (FIGS. 1 e, f). The slab-like nanocrystals exhibit lattice fringes with the spacing measured to be ca. 0.31 nm, which can be assigned to the (111) planes of $CeO_2$ in the fluorite phase (FIG. 1b). X-ray diffraction (XRD) pattern collected for the $Pt_1@CeO_2$ catalyst only shows the $CeO_2$ peaks in the fluorite (Fm3̄m) phase (FIG. 8), where the absence of Pt-phase peaks is consistent with the atomic dispersion of Pt as observed in the STEM images.

Figure 9:
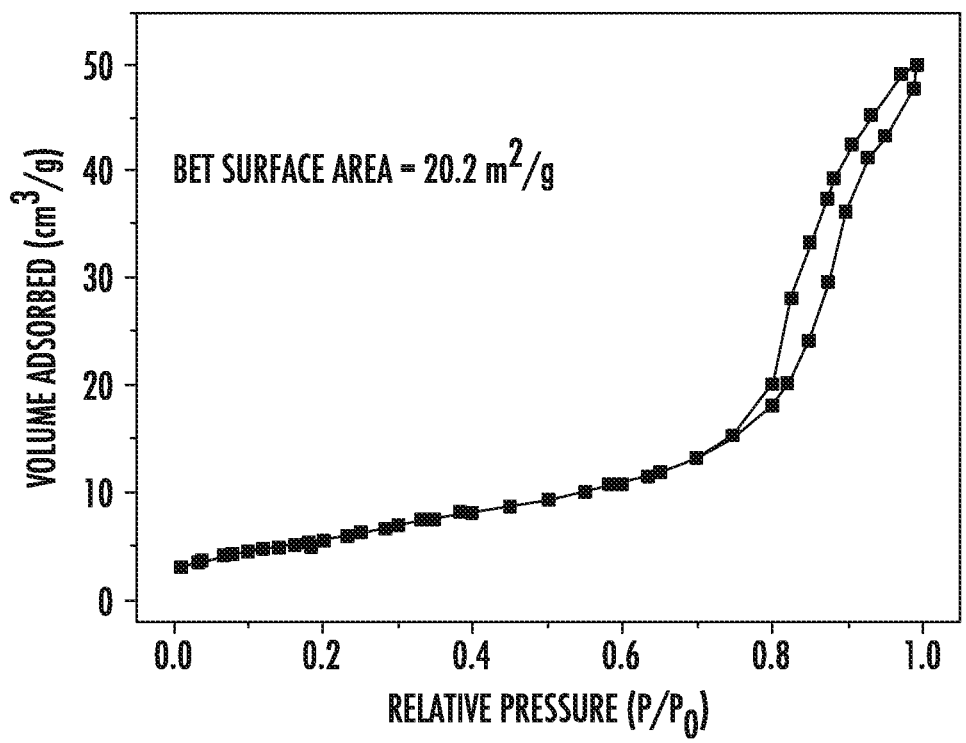
FIG. 9. $N_2$ adsorption and desorption isotherms for $Pt_1@CeO_2$.
Figure 10:
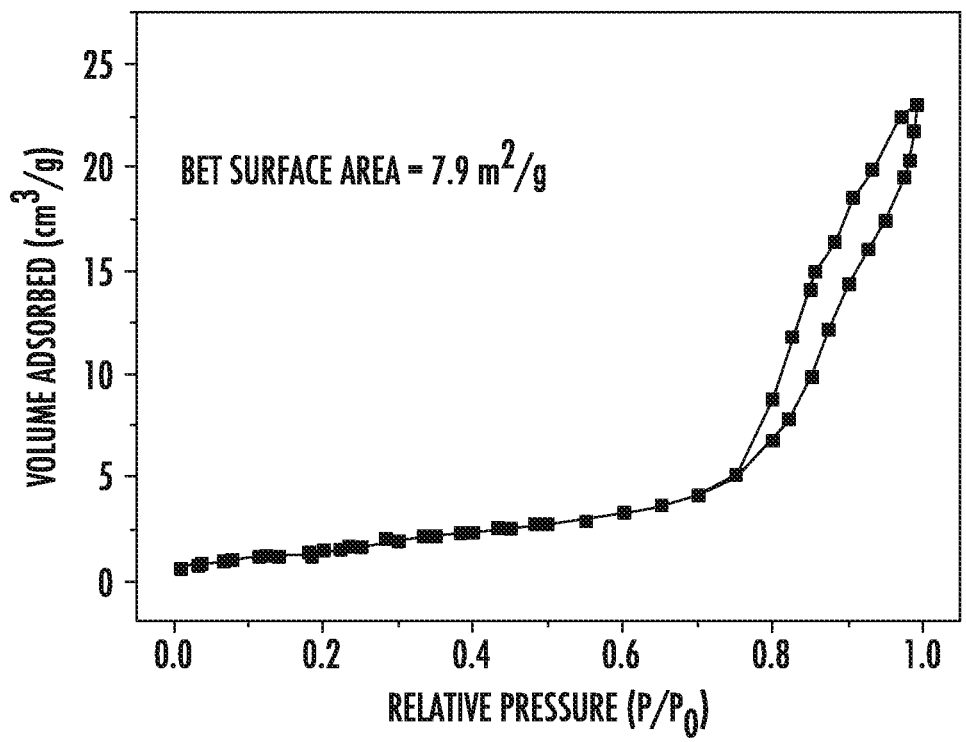
FIG. 10. $N_2$ adsorption and desorption isotherms for $PtNPs/CeO_2$.

As a control, 3 nm Pt nanoparticles were synthesized and deposited on similar $CeO_2$ nanoslabs at the same loading (denoted as $PtNPs/CeO_2$) (FIG. 7). The loadings of Pt on the $Pt_1@CeO_2$ and $PtNPs/CeO_2$ catalysts were measured to be ca. 0.42 and 0.60 wt %, respectively, using inductively coupled plasma-mass spectrometer (ICP-MS). Brunauer-Emmett-Teller (BET) analysis shows that the $Pt_1@CeO_2$ catalyst has a specific surface area of 20.2 $m^2/g$, versus 7.9 $m^2/g$ for $PtNPs/CeO_2$ (FIGS. 9 and 10).

Oxidation state of Pt in the catalysts was characterized by using XPS (FIG. 2). The spectrum collected for $Pt_1@CeO_2$ shows two peaks at the Pt 4f edge with binding energies of 73.7 eV and 76.9 eV, which are assigned to the $4f_{7/2}$ and $4f_{5/2}$ states of $Pt^{2+}$, respectively (FIG. 2a). For $PtNPs/CeO_2$, the Pt 4f doublet exhibits downshift by ~1 eV in binding energy (FIG. 2c). Deconvolution analysis reveals the presence of two additional peaks at 72.2 and 75.7 eV, in addition to the aforementioned two peaks associated with $Pt^{2+}$, which can be assigned to the same spin-orbital split of metallic Pt (Pt). The atomic ratio between $Pt^{2+}$ and $Pt^0$ was estimated to be ~1.5 in the $PtNPs/CeO_2$ catalyst, with the oxidized Pt likely coming from surface oxidation of the Pt nanoparticles during calcination.

The XPS spectra collected at the Ce 3d edge are shown in FIGS. 2 b and d for the two catalysts. As we showed in previous studies, the spectra can be deconvoluted on the basis of two multiplets that correspond to the $3d_{3/2}$ and $3d_{5/2}$ core holes of Ce (denoted as u and v, respectively) and have a spin-orbit splitting of ~18.6 eV. A total of ten peaks can be identified in the present analysis and assigned to five different energy states: $u^0$ (898 eV) and $v^0$ (880 eV) for $Ce(3d^94f^1)-O(2p^6)$, u (901 eV) and v (882 eV) for $Ce(3d^94f^2)-O(2p^4)$, $u^I$ (904 eV) and $v^I$ (885 eV) for $Ce(3d^94f^2)-O(2p^5)$, $u^{II}$ (906 eV) and $v^{II}$ (889 eV) for $Ce(3d^94f^1)-O(2p^5)$ and $u^{III}$ (916 eV) and $v^{III}$ (897 eV) for $Ce(3d^94f^0)-O(2p^6)$. The states marked with $u^0/v^0$ and $u^I/v^I$ are features of $Ce^{3+}$, which was estimated to occupy ~46% and 33% of the Ce species in the $Pt_1@CeO_2$ and $PtNPs/CeO_2$ catalysts, respectively (Table 1).

TABLE 1

Pt and Ce oxidation states derived from the XPS analyses for the $Pt_1@CeO_2$ and $PtNPs/CeO_2$ catalysts.

| Sample | $Pt^0$ % | $Pt^{2+}$ % | $Ce^{3+}$ % | $Ce^{4+}$ % |
|---|---|---|---|---|
| $Pt_1@CeO_2$ | 0 | 100 | 45.7 | 54.3 |
| $PtNPs/CeO_2$ | 40.4 | 59.6 | 32.6 | 67.4 |

These results indicate that the $CeO_2$ nanoslabs employed as support here are rich in Ce defects and oxygen vacancies, which is likely a result of oxygen evolution during the high-temperature (1000° C.) treatment.

The XPS analysis shows that, in the $Pt_1@(CeO_2$ catalysts, Pt was dispersed on the $CeO_2$ support in the oxidized form ($Pt^{2+}$). It was reported that Pt can be emitted as volatile $PtO_x$ above 800° C. in air,[14] which could then re-condense and deposit on the $CeO_2$ support. Ce(III) and oxygen vacancies enriched on the $CeO_2$ substrate represents coordinatively unsaturated, electrophilic sites, which could have attracted and stabilized atomic platinum oxides, e.g., in the form of planar $Pt^{2+}O_4$ clusters.[36] Thereby Pt was favorably dispersed as single-atom species on the $CeO_2$ support.

Figure 3A:
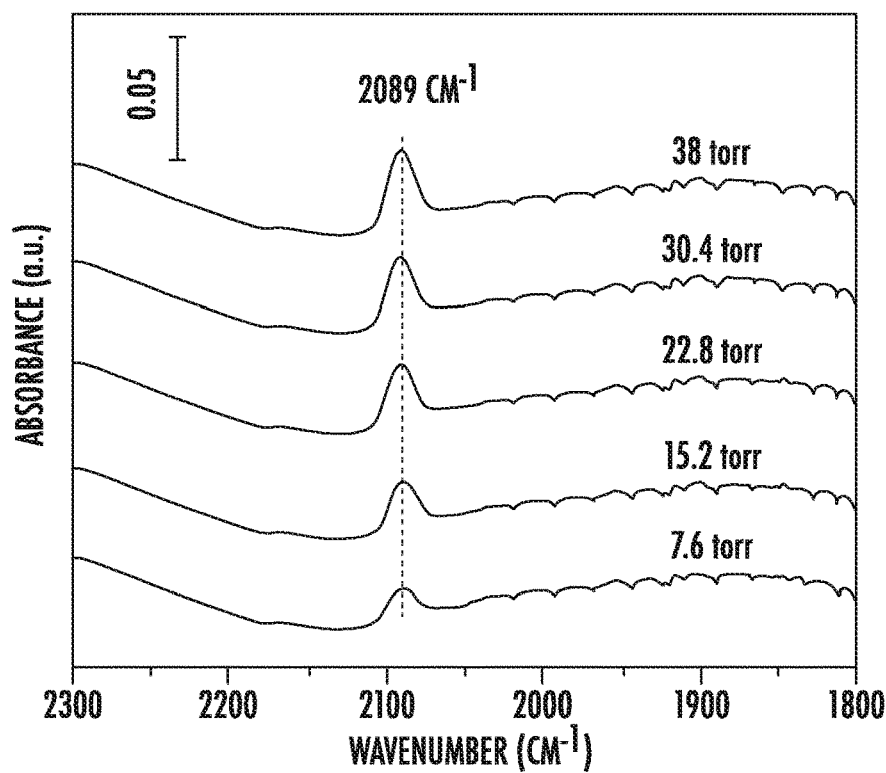
FIG. 3A-3B. DRIFTS of CO chemisorption at different CO partial pressures on (a) $Pt_1@CeO_2$ and (b) $PtNPs/CeO_2$.
Figure 3B:
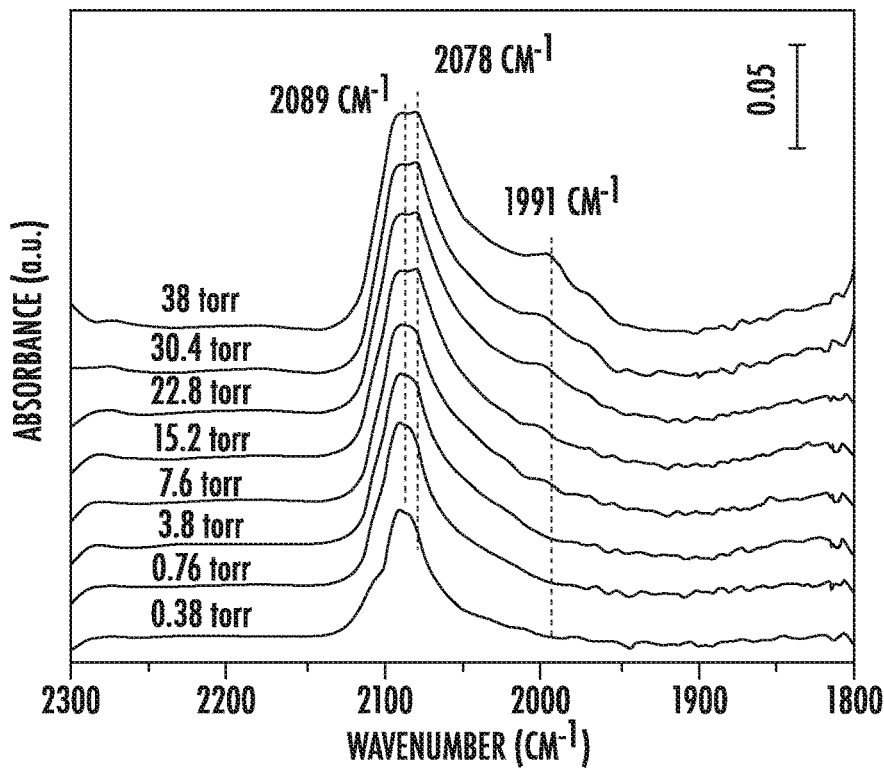

To gain a more extensive evaluation of the atomic dispersion of Pt, the inventors have further performed diffuse reflectance infrared Fourier transform spectroscopy (DRIFTS) analysis of CO adsorption on the $Pt_1@CeO_2$ catalyst. This method has previously been demonstrated to be effective in identification of single Pt atoms on oxide supports. FIG. 3a shows the absorption spectra recorded on the $Pt_1@CeO_2$ catalyst with CO pre-adsorbed at different partial pressures. Only one peak was observed at 2,089 $cm^{-1}$, which can be assigned to the linearly bonded CO ($CO_L$) on $Pt^{\delta+}$.[13] In contrast, the $PtNPs/CeO_2$ catalyst exhibits two additional peaks at 2,078 $cm^{-1}$ and 1,991 $cm^{-1}$, in addition to the $CO_L$ peak at 2,089 $cm^{-1}$ (FIG. 3b). In this case, the peak at 2078 $cm^{-1}$ can be assigned to $CO_L$ on the Pt nanoparticles, with the different peak position from that for the $Pt_1@CeO_2$ catalyst due to the different coordination numbers or oxidation state of surface Pt atoms. The other peak at 1991 $cm^{-1}$ is ascribed to the bridge bonded CO ($CO_B$) on Pt, which is another feature of Pt ensembles with continual surfaces. The absence of the $CO_B$ peak thereby confirms the isolation of Pt sites in the $Pt_1@CeO_2$ catalyst.

Figure 4A:
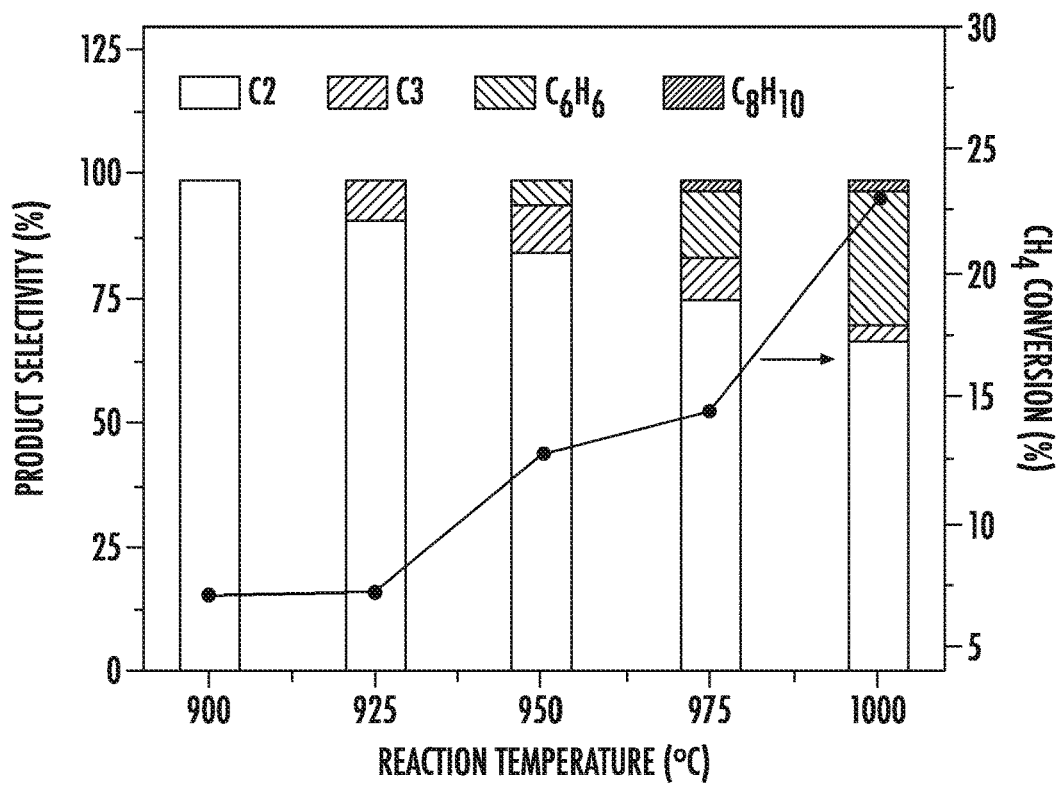
FIG. 4A-4D. Catalytic performance for the nonoxidative $CH_4$ conversion evaluated at 6 L/($g_{cat}$·h). (a) Catalytic activities and selectivities of the $Pt_1@CeO_2$ catalyst as functions of the reaction temperature. Black squares represent $CH_4$ conversion, and the colored histograms for product distributions. Here the light olefins are categorized as $C_2$ (ethane, ethylene and acetylene) and $C_3$ (propane, propylene and propyne) hydrocarbons, with further breakdown of the $C_2$ products shown in (b). (c) Comparison of methane conversion and product distributions at 975° C. over the two catalysts and the controls. (d) Stability test of the $Pt_1@CeO_2$ catalyst performed at 975° C.
Figure 11:
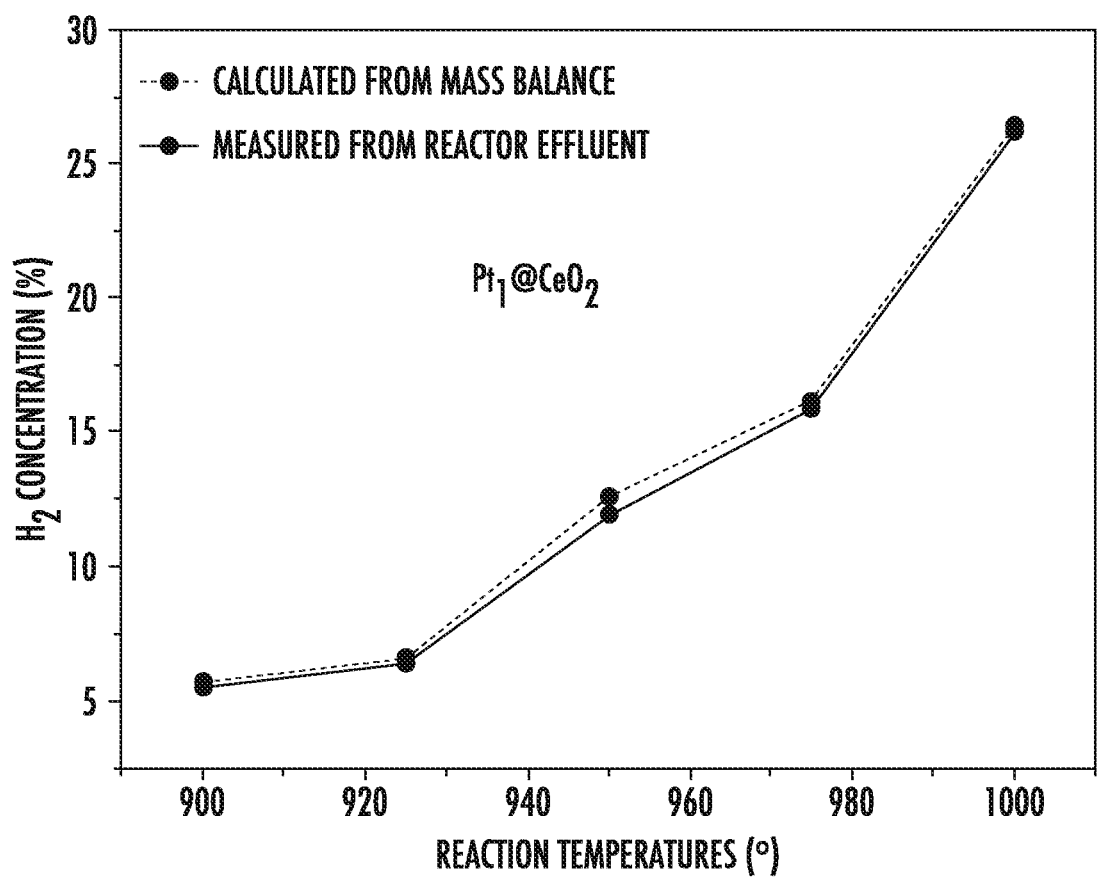
FIG. 11. Hydrogen contents derived from the methane conversion reaction over $Pt_1@CeO_2$: (blue) calculated from mass balance versus (red) measured from the reactor effluents.

The $Pt_1@CeO_2$ catalyst was evaluated for nonoxidative conversion of methane at 900-1000° C. with a space velocity of 6 $L/(g_{cat}·h)$. FIG. 4a summarizes the methane conversion and product distributions in dependence of the reaction temperature. The methane conversion increased with temperature and reached 23.1% at 1,000° C. The selectivity of $C_2$ hydrocarbons exhibited gradual decrease from 98.4% at 900° C. to 66.7% at 1,000° C. The amount of $C_3$ product was rather small and always <10% throughout the investigated temperature range. At temperatures ≥950° C., aromatic products started to appear and the selectivities increased with temperature, achieving 26.6% for benzene and 2.1% for naphthalene at 1,000° C. It is noticed that the amount of hydrogen generated from the methane conversion matches well with the concentrations calculated from the reaction stoichiometries and mass balance by taking the various hydrocarbon products into account (FIG. 11).

The performance of the $Pt_1@CeO_2$ catalyst is noticeably different from the previously reported atomic $Fe@SiO_2$ catalyst, albeit with similar methane conversion (e.g., 12.7% for $Pt_1@CeO_2$ versus ~8% for $Fe@SiO_2$ at 950° C.). The atomic Pt catalyst reported here gave rise to much higher $C_2$ product selectivity, with 84.3% compared to ~47% by $Fe@SiO_2$ at 950° C. In the latter case, the rest products were mainly aromatics (consistently ~50% in total independent of the reaction temperature) and nearly equally distributed between benzene and naphthalene. While the $Pt_1@2CeO_2$ catalyst produced all the three kinds of $C_2$ species, ethylene was the only $C_2$ product from the $Fe@SiO_2$ catalyst. These differences suggest that the $Pt_1@CeO_2$ catalyst may possess distinct catalytic mechanisms, particularly in the C—C coupling steps, from the $Fe@SiO_2$ catalyst where multi-carbon species were believed to form from gas-phase methyl (·$CH_3$) radicals via noncatalytic, thermodynamic equilibrium processes.

Figure 4B:
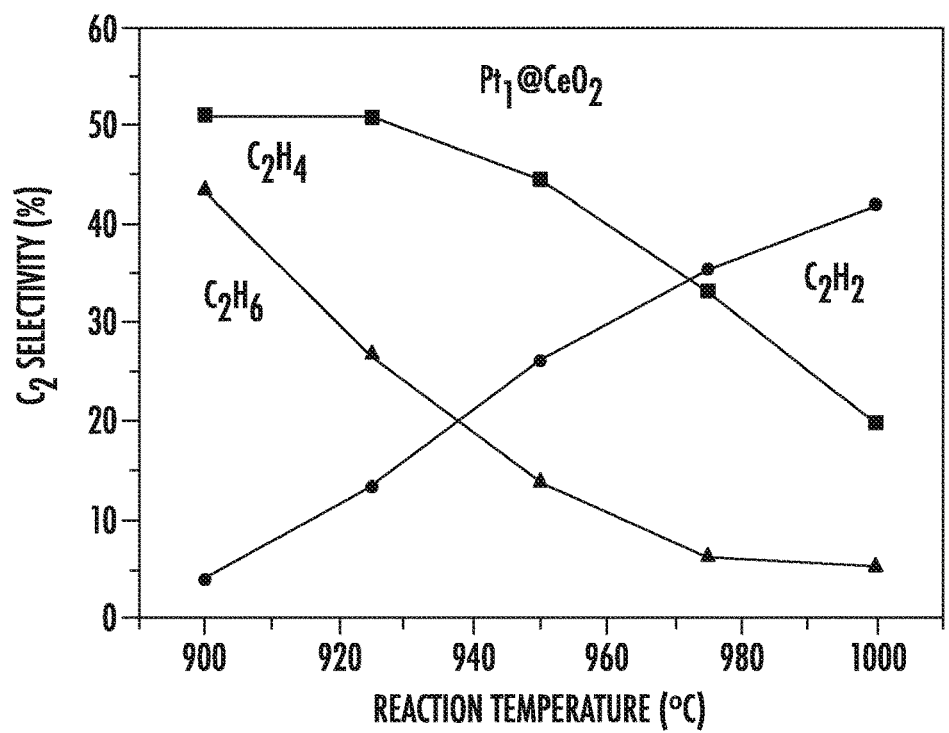
Figure 4C:
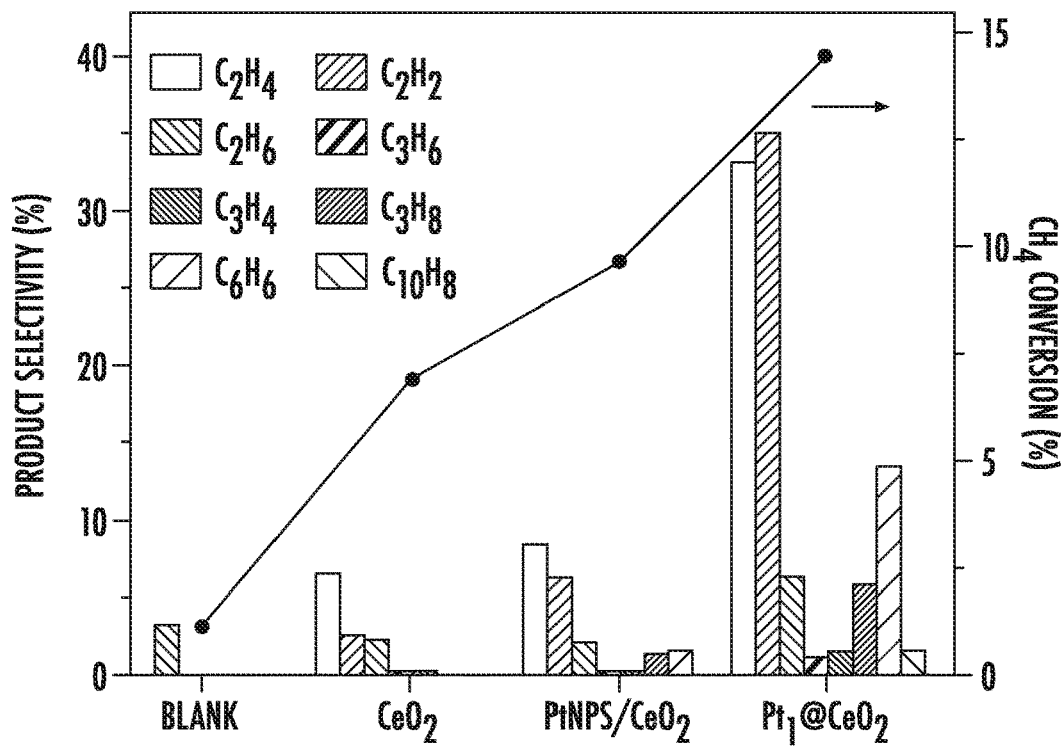
Figure 4D:
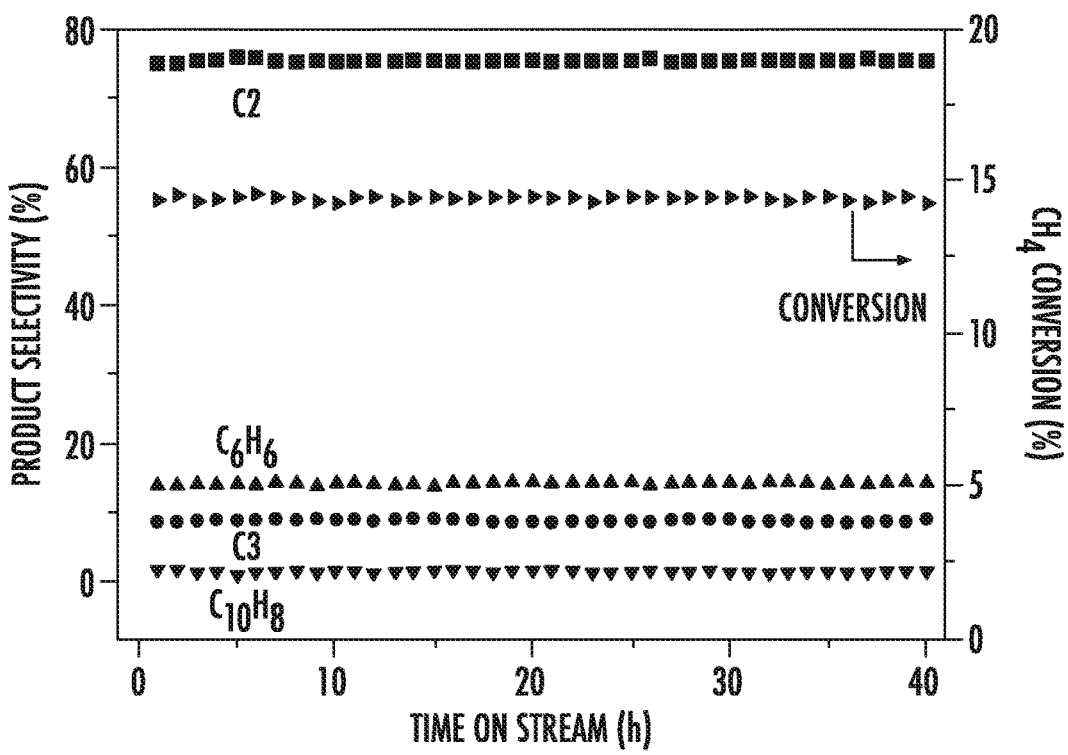
Figure 12:
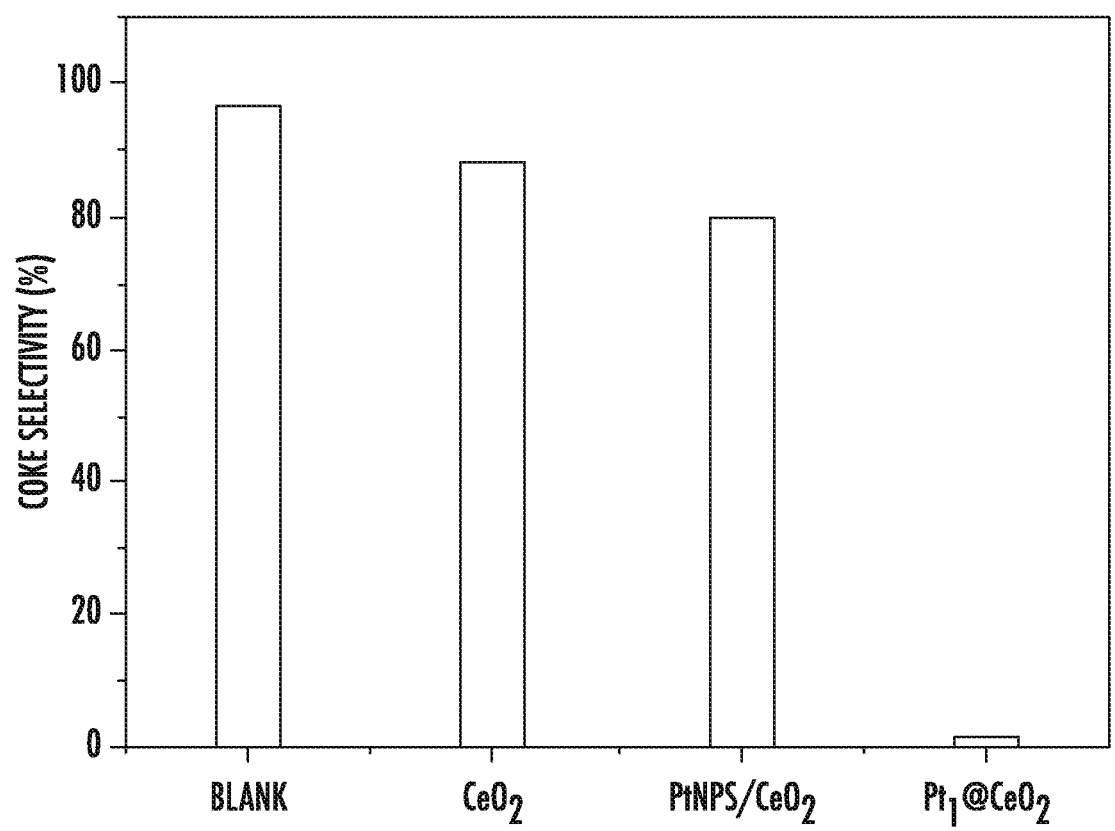
FIG. 12. Estimated proportions of carbon species deposited as coke during the methane conversion over blank reaction tube, bare $CeO_2$ support, $PtNPs/CeO_2$ and $Pt_1@CeO_2$ at 975° C.
Figure 13:
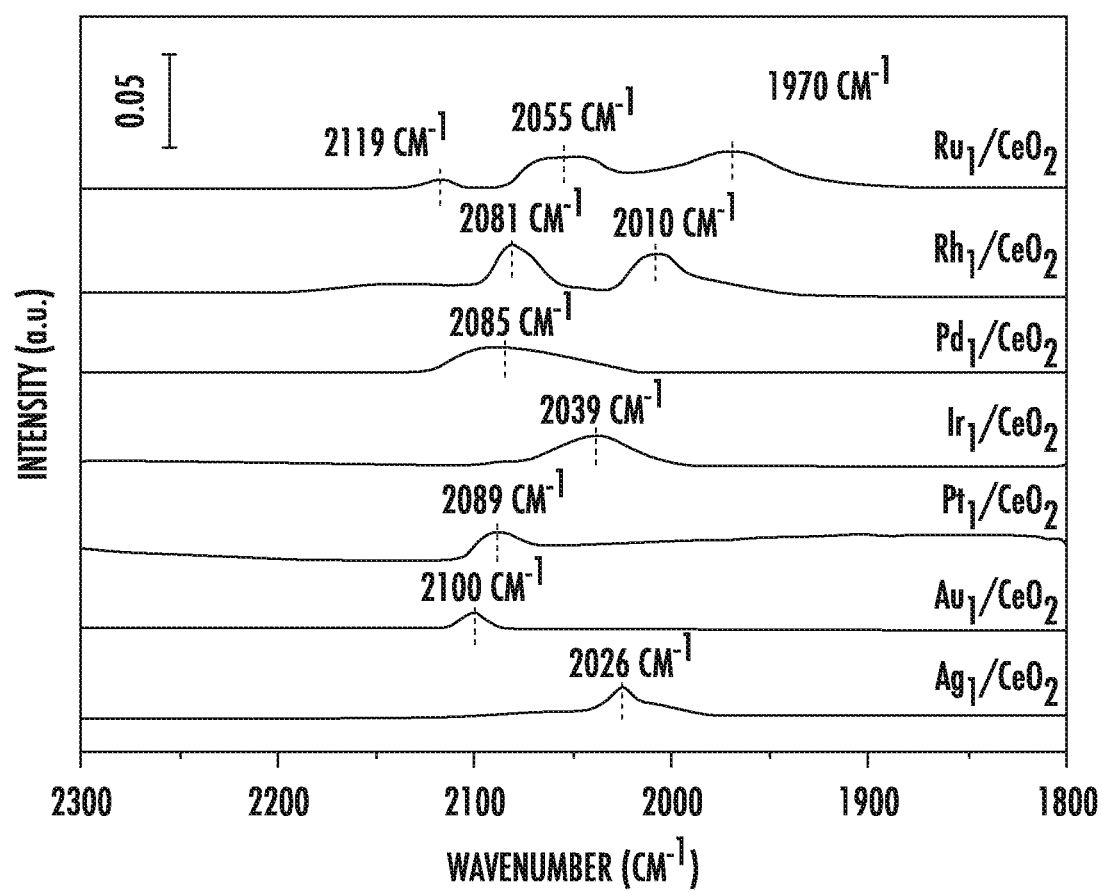
FIG. 13. DRIFTS of CO chemisorption of other single atom noble metal catalysts supported on $CeO_2$, which include Pd, Rh, Ru, Ag, Au and Ir.

Breakdown of the $C_2$ product distributions is further elucidated in FIG. 4b. At relative low temperatures, ethylene and ethane were the two dominant products, with the selectivity measured to be 51.1% and 43.6% at 900° C., respectively. At elevated temperatures, acetylene became more abundant and its selectivity achieved 41.7% at 1,000° C., whereas only 19.8% of ethylene and 5.1% of ethane were left at this temperature. These trends indicate that the $C_2$ products may undergo further dehydrogenation after their formation, the equilibrium of which favors the generation of acetylene at higher temperatures. It is also in line with the observed production of more hydrogen from the methane conversion at higher temperatures (FIG. 11). The atomic Pt catalyst is much superior to its nanoparticulated counterpart for the methane conversion reaction. FIG. 4c provides the comparison of methane conversion and product selectivity for the $Pt_1@CeO_2$ and $PtNPs@CeO_2$ catalysts at 975° C., together with the control in the cases of blank reaction tube and bare $CeO_2$ support. The amount of coke formed during the methane conversion was estimated by the mass balance analysis, with the occupying ratio of carbon species presented separately in the Supporting Information (FIG. 12). It is noticed that even in the blank reaction tube, $CH_4$ had a conversion of 1.1% at this temperature due to the non-catalytic, thermal activation and dehydrogenation, but no hydrocarbons were detected at significant amounts (albeit with some ethane at 3.2% selectivity), suggesting that the converted methane mostly became coke and deposited on the tube wall. The bare $CeO_2$ support exhibited somewhat higher (6.9%) $CH_4$ conversion, but coke was still the dominant (88.3%) product. The PtNPs@CeO$_2$ catalyst raised the CH$_4$ conversion to 9.7% and the selectivities toward ethylene and acetylene reached 8.3% and 6.3%, respectively; however, 79.8% of the carbon atoms ended up in coke which was not quite different from the situation with bare CeO$_2$ support. Both the catalytic activity and selectivity were substantially improved with the Pt$_1$@CeO$_2$ catalyst, achieving 14.4% of methane conversion and 98.5% selectivity toward hydrocarbons. Herein the hydrocarbon products were dominated by ethylene (33.2%) and acetylene (35.1%). The coke formation was suppressed to be only ~1.5% proportion of the carbon atoms derived from methane in this case, which could be ascribed to the carbon deposition on tube wall and/or the CeO$_2$ substrate.

From the above observations, it can be seen that the CeO$_2$ substrate may play an active role in activating methane, as indicated by the considerable conversion of methane on the bare CeO$_2$ substrate. Compared to the bare CeO$_2$ substrate, the incorporation of Pt nanoparticles made insignificant changes to the product distributions, albeit having slightly raised the methane conversion. This finding is consistent with the reported situation on the conventional catalysts with ensembles of Pt atoms, where further oligomerization of the C—C species becomes inevitable on continuous metal surfaces and causes coking. It is only on the Pt$_1$@(CeO$_2$ catalyst that methane is selectively converted into light olefins and aromatics, highlighting the importance of having atomically dispersed active sites in suppression of carbon coking.

Ultimately, durability of the Pt$_1$@CeO$_2$ catalyst was examined by performing prolonged operations of the conversion reaction. It was found that both the conversion and product selectivities were sustainable and did not exhibit any discernible drop after 40 h of reaction at 975° C. (FIG. 4$d$). The high durability does not only confirm the suppression of carbon coking, but also indicates great potential of the nanoceria-supported atomic Pt catalyst for implementation in practical plants.

Methods/Examples

The following Methods/Examples have been included to provide guidance to one of ordinary skill in the art for practicing representative embodiments of the presently disclosed subject matter. In light of the present disclosure and the general level of skill in the art, those of skill can appreciate that the following Methods/Examples are intended to be exemplary only and that numerous changes, modifications, and alterations can be employed without departing from the scope of the presently disclosed subject matter. The following Methods/Examples are offered by way of illustration and not by way of limitation.

1. Materials and Methods

Chemicals. Platinum(IV) chloride (>99.99%), Cerium(III) nitrate hexahydrate (>99.999%), Propionic acid (ACS reagent, ≥99.5%), Ethylene glycol (anhydrous, 99.8%), Borane tert-butylamine (97%), Oleylamine (≥98%) were purchased from Sigma Aldrich. Platinum(II) acetylacetonate (98%) was purchased from ACROS Organics. These chemicals were used as-received without further purification. Deionized water (18.2 MΩ) was collected from an ELGA PURELAB flex apparatus.

Figure 5:
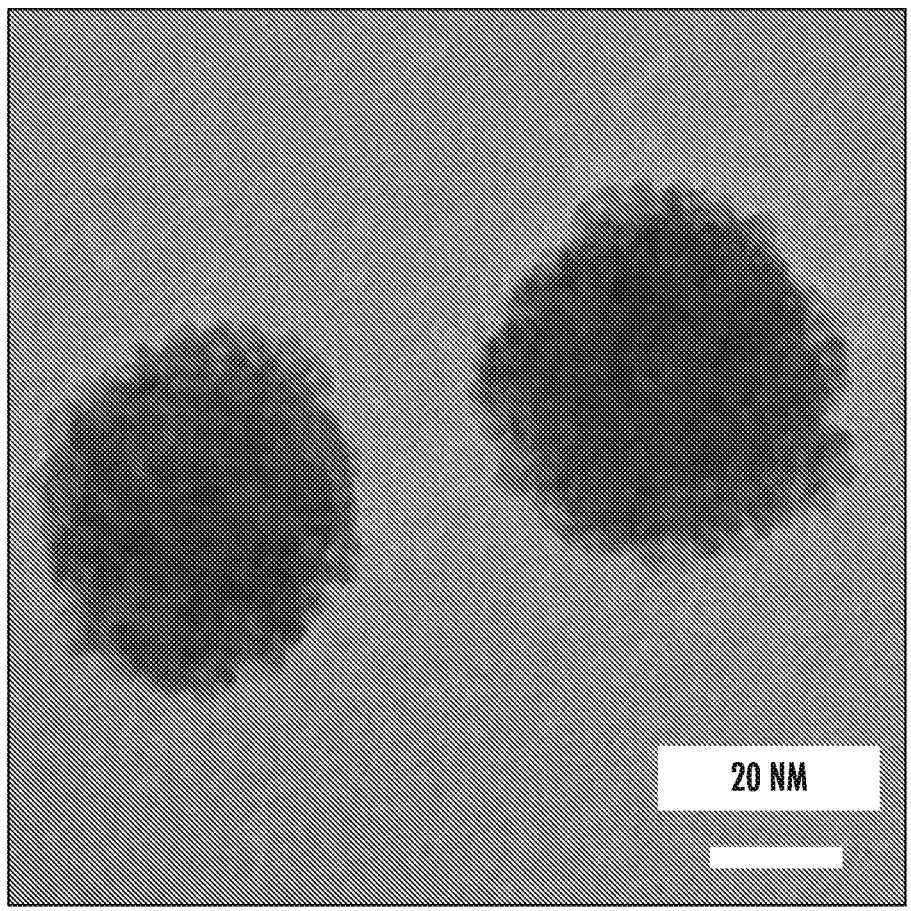
FIG. 5. Representative TEM image of the Pt-impregnated porous $CeO_2$ nanospheres synthesized for the preparation of $Pt_1@CeO_2$.
Figure 6A:
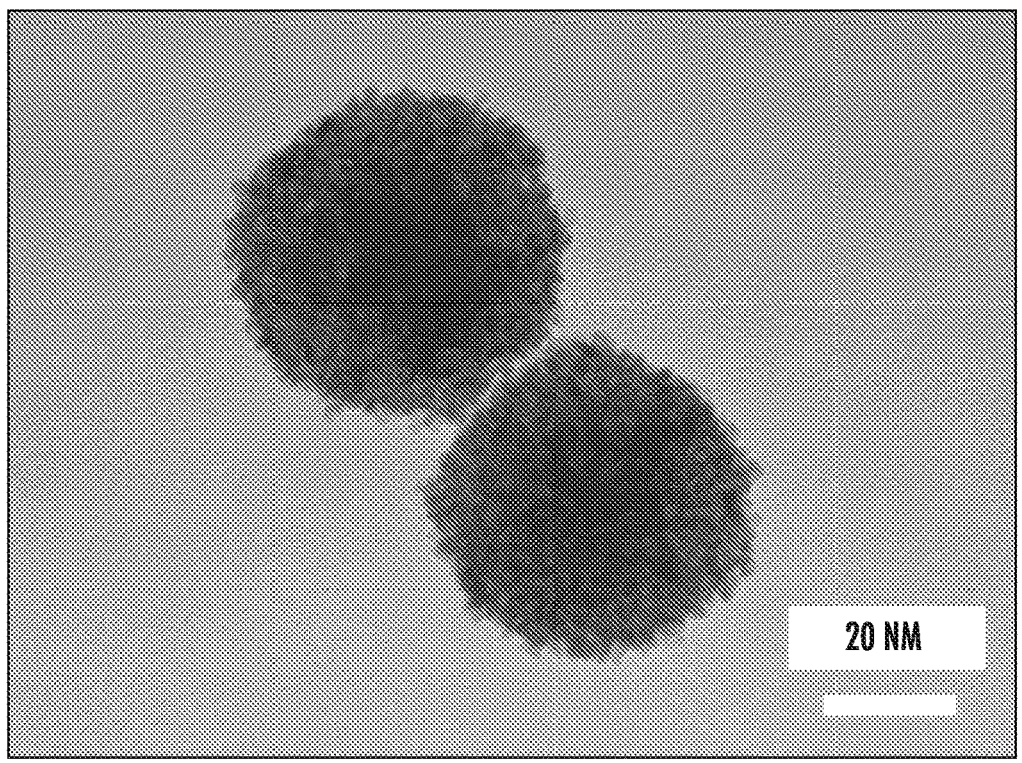
FIG. 6A-6B. Representative TEM images of (a) porous $CeO_2$ nanospheres synthesized without adding $PtCl_4$ and (b) $CeO_2$ nanoslabs obtained by calcination of the porous $CeO_2$ nanospheres at 1000° C.
Figure 6B:
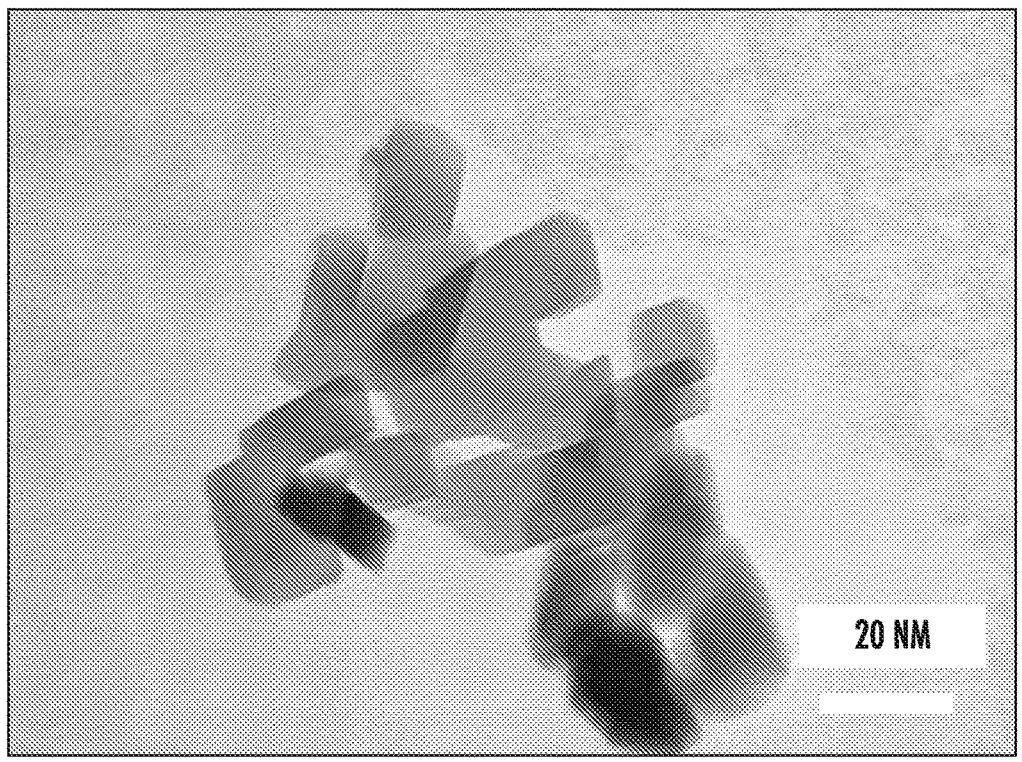
Figure 7A:
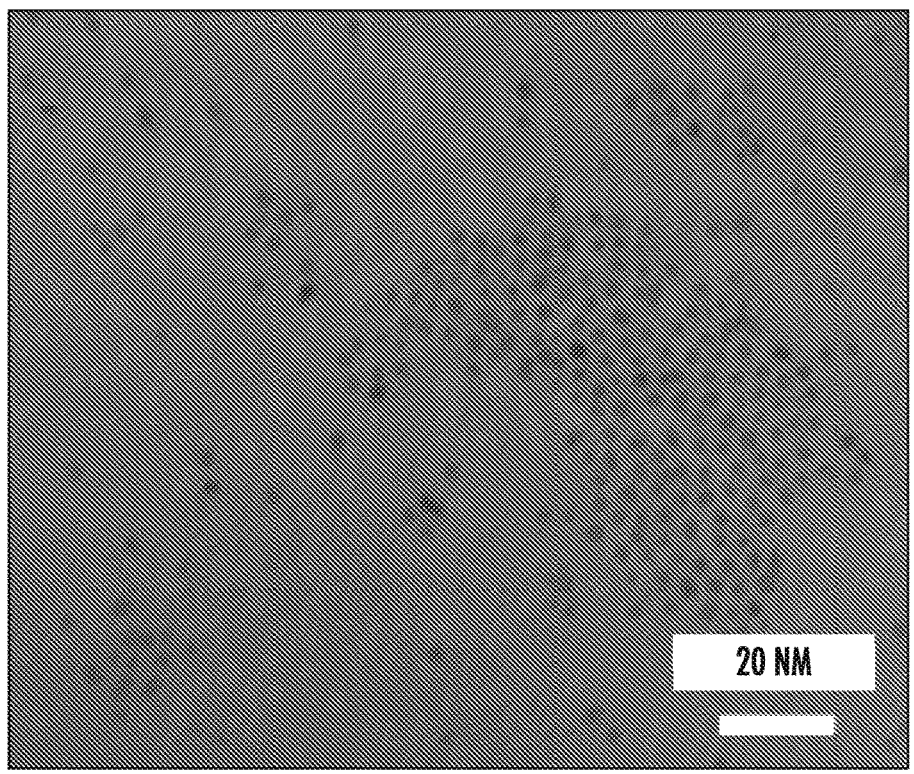
FIG. 7A-7F. (a) Representative TEM image of Pt nanoparticles. (b-e) Representative TEM images of $PtNPs/CeO_2$. (f) Size distribution of Pt nanoparticles in the $PtNPs/CeO_2$ catalyst.
Figure 7B:
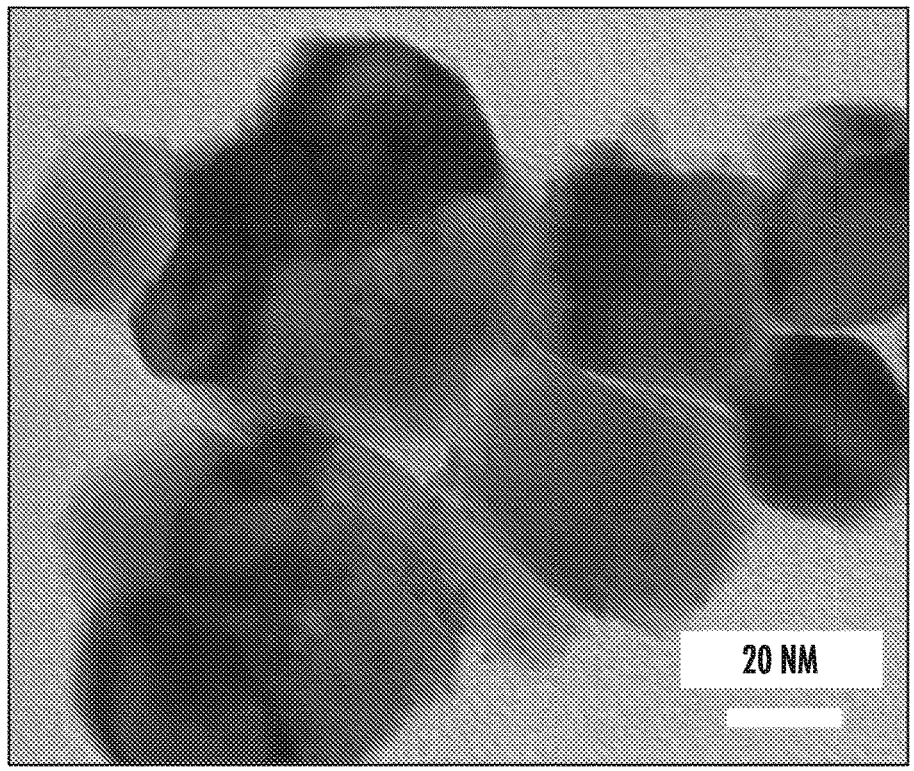
Figure 7C:
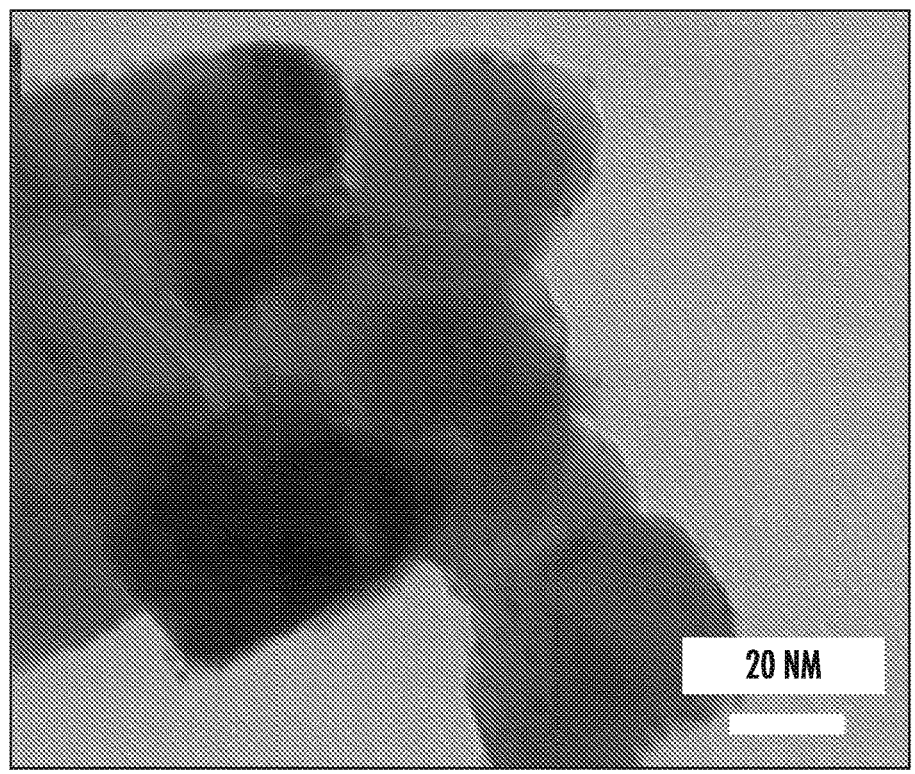
Figure 7D:
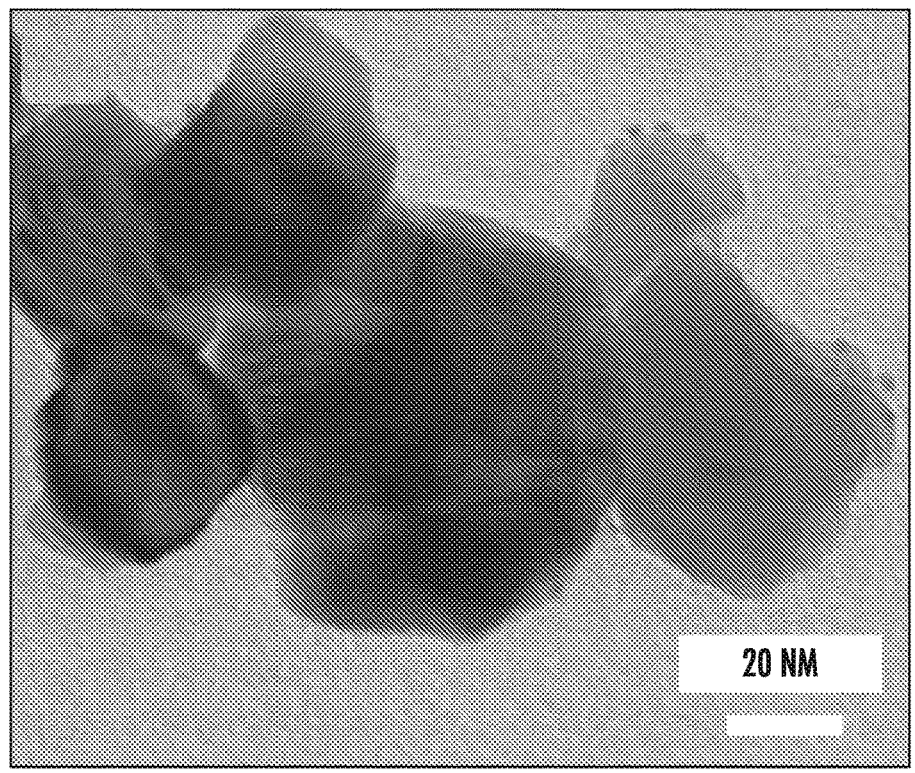
Figure 7E:
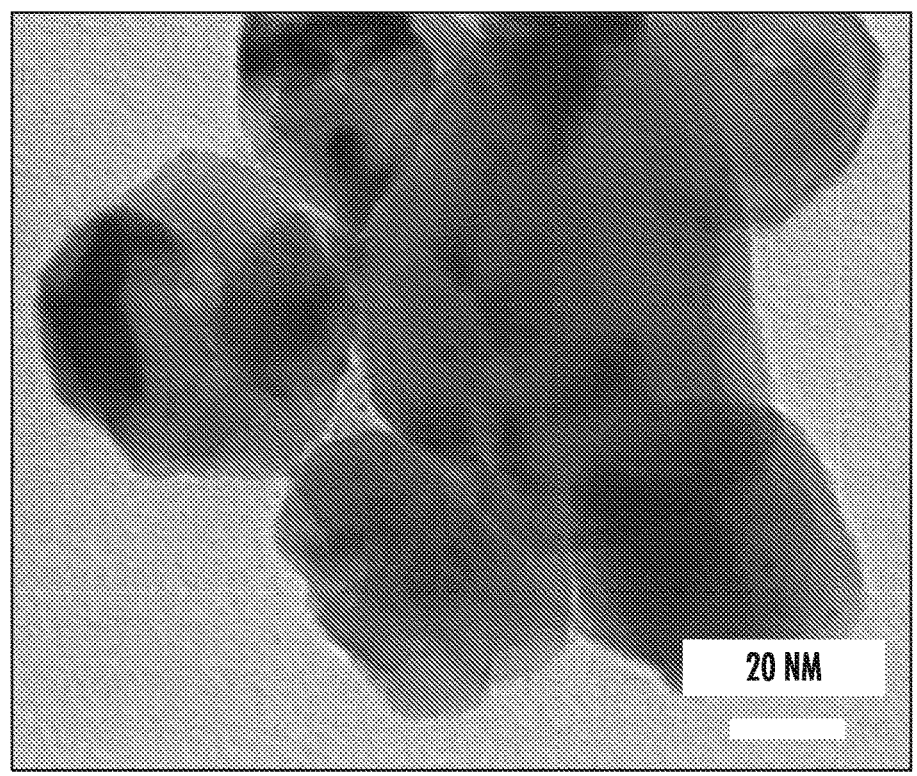
Figure 7F:
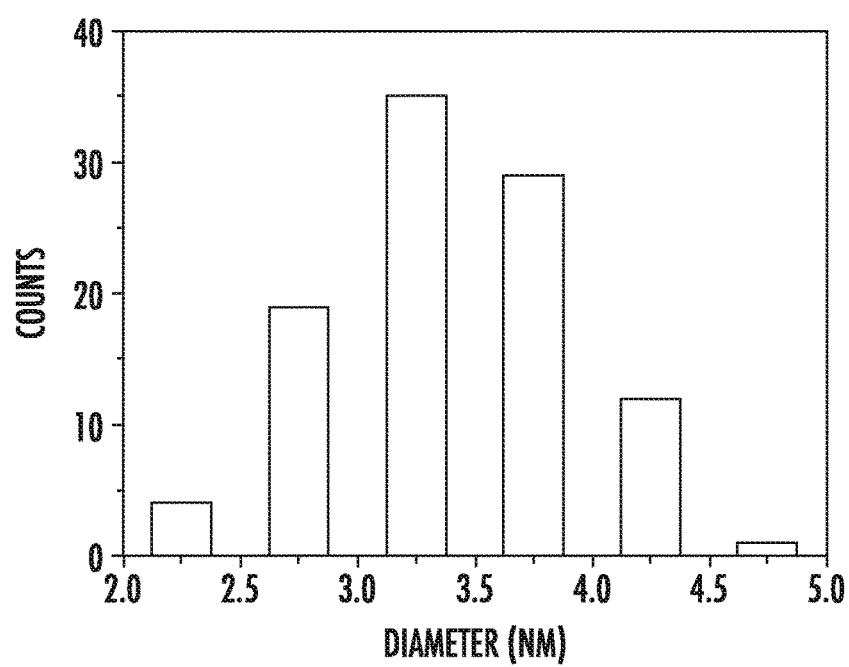

Synthesis. For the preparation of Pt$_1$@CeO$_2$, Pt-impregnated porous CeO$_2$ nanospheres were first synthesized by modifying the method reported in the literature.[1] Typically, 1.0 g Ce(NO$_3$)$_3$.6H$_2$O with 6.90 mg of PtCl$_4$ was dissolved in 1 mL deionized water. To this solution 1 mL of propionic acid and 30 mL of ethylene glycol were added with stirring. The formed uniform solution was sealed in an autoclave and heated at 160° C. for 3 hours. The product was collected by centrifugation (10000 rpm, 10 minutes) and washed thoroughly with DI water and dry ethanol. It was dried at 110° C. in air for 5 h and at 300° C. for another 2 h to remove any residual water or organics. The obtained porous nanospheres (FIG. 5) were then calcined in air at 1000° C. for 2 h, which converted the nanospheres into crystalline nanoslabs with atomically dispersed Pt (see the TEM images shown in the main text, FIG. 1). CeO$_2$ nanoslabs were synthesized in a similar way without adding the Pt salt (FIG. 6).

PtNPs/CeO$_2$ was also prepared as a control to the atomic Pt catalyst (FIG. 7). Pt nanoparticles were synthesized in an organic solution phase by following the reported method.[2] Basically, 0.2 mmol of Pt(acac)$_2$ was dissolved in 15 mL of oleylamine, stirred at 800 rpm in Ar atmosphere. The solution was first raised to 70° C. and kept at this temperature for 10 min, to which a mixture of borane tert-butylamine complex (BTB) (0.4 mmol) and oleyamine (2 mL) was injected. The solution was further stirred at 70° C. for 30 min and then cooled down to room temperature. The product was collected by adding 250 mL of methanol and centrifugation, which was re-dispersed in 20 mL of hexane. To deposit the Pt nanoparticles onto CeO$_2$, 1 g of CeO$_2$ nanoslabs and the 5.03 mg of Pt nanoparticles were mixed in 50 mL of ethanol. The obtained mixture was rigorously stirred for 45 min at room temperature. After that, the solvent was removed by using a rotary evaporator. The obtained solid was dried in vacuum and then calcined at 300° C. in air for 2 h.

Characterizations. X-ray diffraction (XRD) patterns were obtained from a PANalytical X'Pert$^3$ X-ray diffractometer equipped with a Cu Kα radiation source (λ=1.5406 Å). Nitrogen adsorption measurements were measured on a Micromeritics ASAP 2010 instrument with the samples degassed under vacuum at 300° C. for 4 h. Specific surface area (SSA) was calculated using the Brunauer-Emmett-Teller (BET) theory. The Pt contents were determined by inductively coupled plasma mass spectrometry (ICP-MS) using a PerkinElmer Elan DRC II Quadrupole ICP-MS after dissolution of the materials in the mixture of aqua regia and hydrogen peroxide.

TEM images were recorded on a Philips EM 420 worked at 120 kV. The HAADF images were acquired using a 22-mrad-probe convergence semi-angle and a 90-mrad inner-detector angle at 200 KV, using an aberration-corrected JEOL JEM-ARM200CF STEM. The average particle size and distribution were determined by ImageJ software. The average particle size and distribution were determined by ImageJ software.

X-ray photoelectron spectroscopy (XPS) data were obtained on a Shimadzu/Kratos Axis Ultra Dld spectrometer with Al Kα radiation as the excitation source. The adventitious carbonaceous C 1s line (284.6 eV) was used to calibrate the binding energy (BE). The XPS spectra were deconvoluted using Origin 9.0 software with Shirley background subtraction and a Gaussian-Lorentzian functions.

FTIR spectra for CO adsorption were recorded on a Nicolet 6700 spectrometer equipped with a mercury cadmium telluride (MCT) detector cooled by liquid N$_2$. The in situ cell was fitted with ZnS windows and a heating cartridge. Before CO adsorption, samples were evacuated at 200° C. for 2 h, and then cooled to 25° C. for CO adsorption. Spectra were collected at 25° C. with a resolution of 4 cm$^{-1}$ and accumulation of 100 scans for each sample.

Catalytic studies. Catalytic nonoxidative conversion of CH$_4$ was conducted in a fixed-bed flow reactor at atmospheric pressure.[3] Before reaction, a pretreatment was applied: 0.2 g catalyst (40-60 mesh) was loaded into a microflow quartz reactor (7 mm i.d.), heated to 110° C. at a rate of 5° C./min under He (50 mL/min), and held at 110° C. for 1 h. After pretreatment, the temperature was increased to 900° C. under He and the gas flow was then switched to 1% $CH_4$/He (20 mL min$^{-1}$, space velocity=6 L/($g_{cat}$ h)). The reaction temperature was increased stepwise from 900° C. to 1000° C., and the reaction was carried out at each temperature until the conversion reached constant. To determine the conversions of reactants and the formation of products, a gas chromatograph (GC-2010 plus, Shimadzu) equipped with a SH-Rt-Q-BOND column and a BID detector were employed. All of the lines between the reactor outlet and GC sampling loop inlet were heat-traced to 90° C. to prevent product condensation. Methane conversion, hydrocarbon product selectivity, coke deposition selectivity and $H_2$ concentrations were calculated according to the mass balance, following previously reported methods.[4,5]

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A single atom catalyst comprising:
   $CeO_2$ nanoparticles impregnated with individual noble metal atoms; and
   wherein an atomic ratio of a $Ce^{4+}$ oxidation state to a $Ce^{3+}$ oxidation state is 1.188.

2. The single atom catalyst of claim 1 wherein the noble metal atoms are selected from the group consisting of Pt, Pd, Rh, Ru, Ag, Au, Ir, and a combination thereof.

3. The single atom catalyst of claim 2, wherein the noble metal atoms consist of Pt.

4. The single atom catalyst of claim 3, wherein the platinum is present only in a $Pt^{2+}$ oxidation state.

5. The single atom catalyst of claim 3, wherein a content of Pt is from about 0.42 wt % to about 0.50 wt % of a total weight of the single atom catalyst.

6. The single atom catalyst of claim 3, wherein the Pt is in an oxidized form.

7. The single atom catalyst of claim 1, wherein the single atom catalyst has a particle size of from about 15 nm to about 40 nm.

8. The single atom catalyst of claim 1, comprising a specific surface area in the range of 5 m$^2$/g to 40 m$^2$/g.

9. The single atom catalyst of claim 1, comprising binding energies in a range of 50 eV to 90 eV.

10. A single atom catalyst comprising:
    $CeO_2$ nanoparticles impregnated with individual platinum atoms; and
    binding energies in a range of 50 eV to 90 eV; and
    wherein an atomic ratio of a $Ce^{4+}$ oxidation state to a $Ce^{3+}$ oxidation state is 1.188.

* * * * *